United States Patent
Cameron et al.

(10) Patent No.: US 9,943,111 B2
(45) Date of Patent: Apr. 17, 2018

(54) METHODS AND SYSTEMS FOR VAPOR COOLING

(71) Applicant: Lunatech, LLC, Encino, CA (US)

(72) Inventors: John Cameron, Encino, CA (US); Dean Becker, Fairhope, AL (US); Gene Fein, Oxnard, CA (US)

(73) Assignee: LUNATECH, LLC, Encino, CA (US)

( * ) Notice: Subject to any disclaimer, the term of this patent is extended or adjusted under 35 U.S.C. 154(b) by 44 days.

(21) Appl. No.: 15/252,832

(22) Filed: Aug. 31, 2016

(65) Prior Publication Data

US 2017/0055588 A1 Mar. 2, 2017

Related U.S. Application Data

(60) Provisional application No. 62/212,411, filed on Aug. 31, 2015.

(51) Int. Cl.
| | |
|---|---|
| *A24F 47/00* | (2006.01) |
| *A24F 1/22* | (2006.01) |
| *H05B 1/02* | (2006.01) |
| *A61M 11/00* | (2006.01) |
| *H05B 3/44* | (2006.01) |

(52) U.S. Cl.
CPC ............ *A24F 47/008* (2013.01); *A24F 1/22* (2013.01); *A61M 11/00* (2013.01); *H05B 1/0244* (2013.01); *H05B 3/44* (2013.01); *H05B 2203/021* (2013.01); *H05B 2203/022* (2013.01)

(58) Field of Classification Search
CPC .................................................. A24F 47/008
USPC ........................................................ 131/328
See application file for complete search history.

(56) References Cited

U.S. PATENT DOCUMENTS

| | | | | |
|---|---|---|---|---|
| 7,052,468 | B2* | 5/2006 | Melker | G01N 29/022 600/529 |
| 7,954,730 | B2* | 6/2011 | Ng | B05B 17/0646 239/102.1 |
| 8,478,913 | B2* | 7/2013 | Terlizzi | G06F 21/85 340/5.8 |
| 8,757,147 | B2 | 6/2014 | Terry et al. | |
| 8,820,330 | B2* | 9/2014 | Bellinger | A61M 11/041 128/202.21 |
| 8,851,083 | B2* | 10/2014 | Oglesby | A61M 11/047 131/271 |
| 8,955,522 | B1 | 2/2015 | Bowen et al. | |
| 9,408,416 | B2 | 8/2016 | Monsees et al. | |
| 9,498,002 | B1 | 11/2016 | Lars Kristian Soreide | |
| 9,516,053 | B1* | 12/2016 | Muddu | H04L 63/1425 |
| 9,585,981 | B2 | 3/2017 | Wynalda, Jr. | |
| 2005/0016550 | A1* | 1/2005 | Katase | A24F 47/002 131/194 |
| 2011/0036346 | A1* | 2/2011 | Cohen | A61M 15/0065 128/200.14 |
| 2014/0060552 | A1* | 3/2014 | Cohen | A24F 47/008 131/273 |

(Continued)

*Primary Examiner* — Abdullah Riyami
*Assistant Examiner* — Nader Alhawamdeh
(74) *Attorney, Agent, or Firm* — Hankin Patent Law, APC; Susan L. McCain; Sergio Becerra

(57) ABSTRACT

Disclosed are methods, systems, and apparatuses for vapor cooling. The methods and systems can be used in conjunction with all vaping devices including e-cigarettes, hybrid communication device electronic vapor devices, robotic vapor devices, modified vapor devices "mods," electronic vapor devices, and the like.

18 Claims, 22 Drawing Sheets

(56) References Cited

U.S. PATENT DOCUMENTS

| | | | |
|---|---|---|---|
| 2015/0208729 A1* | 7/2015 | Monsees | A24F 47/008 131/329 |
| 2015/0237918 A1* | 8/2015 | Liu | A24F 47/008 131/328 |
| 2015/0257447 A1* | 9/2015 | Sullivan | A24F 47/008 131/329 |
| 2016/0021934 A1* | 1/2016 | Cadieux | A24F 47/008 131/328 |
| 2016/0089508 A1* | 3/2016 | Smith | A61M 15/06 128/200.16 |
| 2016/0109115 A1* | 4/2016 | Lipowicz | F22B 1/282 392/395 |
| 2017/0006917 A1* | 1/2017 | Alvarez | A24F 47/008 |
| 2017/0042252 A1* | 2/2017 | Takeuchi | A24F 47/00 |
| 2017/0136193 A1* | 5/2017 | Cameron | A61M 11/042 |
| 2017/0136194 A1* | 5/2017 | Cameron | A61M 11/042 |
| 2017/0182267 A1* | 6/2017 | Cameron | A61M 11/042 |

\* cited by examiner

METHODS AND SYSTEMS FOR VAPOR COOLING

CROSS REFERENCE TO RELATED PATENT APPLICATION

This application claims priority to U.S. Provisional Application No. 62/212,411 filed Aug. 31, 2015, here incorporated by reference in its entirety.

BACKGROUND

Consumers utilize electronic vapor cigarettes, pipes, and modified vapor devices to enjoy what is commonly known as "vaping." Vaping is an increasingly popular market segment, which has been, and continues to, steadily gaining market share over the last several years. Various types of personal vaporizers are known in the art. In general, such vaporizers are characterized by heating a solid to a smoldering point, vaporizing a liquid by heat, or nebulizing a liquid by heat and/or by expansion through a nozzle. Such devices are designed to release aromatic materials in the solid or liquid while avoiding high temperatures of combustion and associated formation of tars, carbon monoxide, or other harmful byproducts. The smoothness sensation of inhaling vapor is a well-known positive desire and positive attribute of vaping users. It would be desirable, therefore, to develop new technologies for enhancing the smoothness sensation experienced by users.

SUMMARY

This summary and the following detailed description should be interpreted as complementary parts of an integrated disclosure, which parts may include redundant subject matter and/or supplemental subject matter. An omission in either section does not indicate priority or relative importance of any element described in the integrated application. Differences between the sections may include supplemental disclosures of alternative embodiments, additional details, or alternative descriptions of identical embodiments using different terminology, as should be apparent from the respective disclosures. It is to be understood that both the following general description and the following detailed description are exemplary and explanatory only and are not restrictive.

In an aspect, disclosed, are systems, methods, and devices for cooling heated vapor by application of a cooling mechanism for the vapor within an electronic vapor device. In an aspect, disclosed are methods comprising receiving a heated vapor into a chamber, receiving air into a cooling element to generate cooled air, providing the cooled air into the chamber, mixing the heated vapor and the cooled air, generating cooled vapor and expelling the cooled vapor through an exhaust port. In another aspect, methods are disclosed comprising receiving a heated vapor into a cooling element and expelling the cooled vapor through an exhaust port.

In an aspect, disclosed is an apparatus comprising an air intake, a vapor output, and a container for storing a vaporizable material. The apparatus can further comprise a mixing chamber coupled to the air intake for receiving air, the container for receiving the vaporizable material, and a heating element configured for heating the vaporizable material and the received air to generate a heated vapor. The apparatus can further comprise a cooling element coupled to the mixing chamber, configured for receiving and cooling the heated vapor and providing the cooled vapor to the vapor output.

In an aspect, disclosed is an apparatus comprising an air intake, a vapor output, and a container for storing a vaporizable material. The apparatus can further comprise a mixing chamber coupled to the air intake for receiving air, the container for receiving the vaporizable material, and a heating element configured for heating the vaporizable material and the received air to generate a heated vapor and a cooling element coupled to the air intake, configured for receiving and cooling air and providing the cooled air to the vapor output wherein the cooled air mixes with the heated vapor, resulting in cooled vapor.

The cooling functionality described herein represents new ground in the electronic vapor device landscape and may be termed by various cooling descriptive terms as well as 'virtual menthol'.

To the accomplishment of the foregoing and related ends, one or more examples comprise the features hereinafter fully described and particularly pointed out in the claims. The following description and the annexed drawings set forth in detail certain illustrative aspects and are indicative of but a few of the various ways in which the principles of the examples may be employed. Other advantages and novel features will become apparent from the following detailed description when considered in conjunction with the drawings and the disclosed examples, which encompass all such aspects and their equivalents.

BRIEF DESCRIPTION OF THE DRAWINGS

The features, nature, and advantages of the present disclosure will become more apparent from the detailed description set forth below when taken in conjunction with the drawings, in which like reference characters are used to identify like elements correspondingly throughout the specification and drawings.

DETAILED DESCRIPTION

Figure 1:
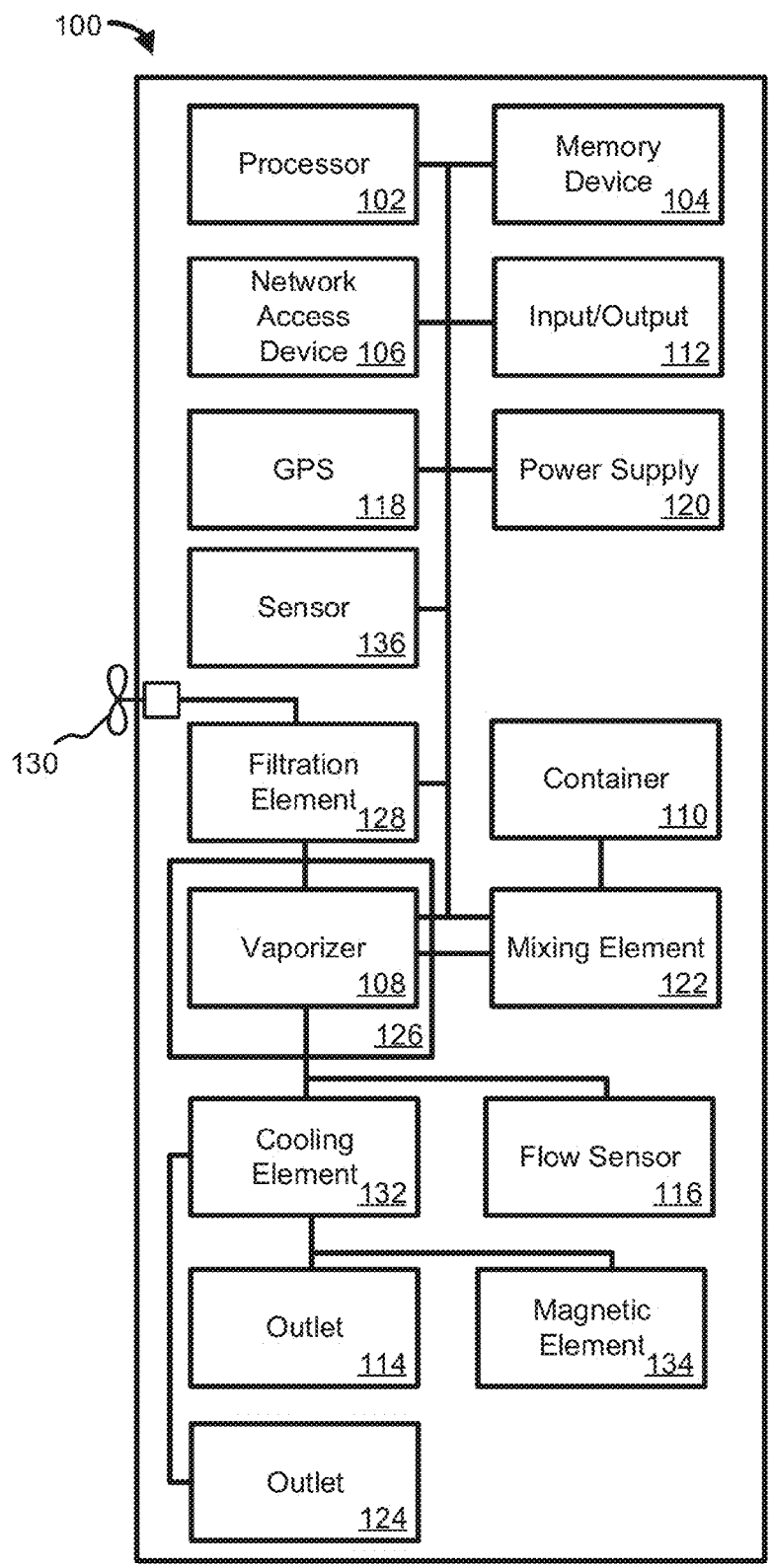
FIG. 1 illustrates a block diagram of an exemplary electronic vapor device.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Various aspects are now described with reference to the drawings. In the following description, for purposes of explanation, numerous specific details are set forth in order to provide a thorough understanding of one or more aspects. It may be evident, however, that the various aspects may be practiced without these specific details. In other instances, well-known structures and devices are shown in block diagram form in order to facilitate describing these aspects.

Disclosed are methods, systems, and apparatuses for vapor cooling. The methods and systems can be used in conjunction with all vaping devices including an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like.

A benefit of the disclosed methods and systems is the creation of additional smoothness via the cooling of vapor prior to inhalation. As the user begins the vaping process the cooling process can also begin. In an aspect, a cooling element can cool the air or space to be combined with heated vapor adjacent to the user inhalation point of the device. In another aspect, heated vapor can be cooled at any point in the device, cooled multiple times, cooled by varying degrees, or heated-cooled-heated and re-cooled, etc., on the way to an inhalation point.

FIG. 1 is a block diagram of an exemplary electronic vapor device 100 as described herein. The electronic vapor device 100 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vapor device 100 can comprise any suitable housing for enclosing and protecting the various components disclosed herein. The vapor device 100 can comprise a processor 102. The processor 102 can be, or can comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 can be coupled (e.g., communicatively, operatively, etc. . . . ) to auxiliary devices or modules of the vapor device 100 using a bus or other coupling. The vapor device 100 can comprise a power supply 110. The power supply 110 can comprise one or more batteries and/or other power storage device (e.g., capacitor) and/or a port for connecting to an external power supply. For example, an external power supply can supply power to the vapor device 100 and a battery can store at least a portion of the supplied power. The one or more batteries can be rechargeable. The one or more batteries can comprise a lithium-ion battery (including thin film lithium ion batteries), a lithium ion polymer battery, a nickel-cadmium battery, a nickel metal hydride battery, a lead-acid battery, combinations thereof, and the like. In an aspect, the power supply 110 can receive power via a power coupling to a case, wherein the vapor device 100 is stored in the case.

The vapor device 100 can comprise a memory device 104 coupled to the processor 102. The memory device 104 can comprise a random access memory (RAM) configured for storing program instructions and data for execution or processing by the processor 102 during control of the vapor device 100. When the vapor device 100 is powered off or in an inactive state, program instructions and data can be stored in a long-term memory, for example, a non-volatile magnetic optical, or electronic memory storage device (not shown). Either or both of the RAM or the long-term memory can comprise a non-transitory computer-readable medium storing program instructions that, when executed by the processor 102, cause the vapor device 100 to perform all or part of one or more methods and/or operations described herein. Program instructions can be written in any suitable high-level language, for example, C, C++, C# or the Java™, and compiled to produce machine-language code for execution by the processor 102.

In an aspect, the vapor device 100 can comprise a network access device 106 allowing the vapor device 100 to be coupled to one or more ancillary devices (not shown) such as via an access point (not shown) of a wireless telephone network, local area network, or other coupling to a wide area network, for example, the Internet. In that regard, the processor 102 can be configured to share data with the one or more ancillary devices via the network access device 106. The shared data can comprise, for example, usage data and/or operational data of the vapor device 100, a status of the vapor device 100, a status and/or operating condition of one or more the components of the vapor device 100, text to be used in a message, a product order, payment information, and/or any other data. Similarly, the processor 102 can be configured to receive control instructions from the one or more ancillary devices via the network access device 106. For example, a configuration of the vapor device 100, an operation of the vapor device 100, and/or other settings of the vapor device 100, can be controlled by the one or more ancillary devices via the network access device 106. For example, an ancillary device can comprise a server that can provide various services and another ancillary device can comprise a smartphone for controlling operation of the vapor device 100. In some aspects, the smartphone or another ancillary device can be used as a primary input/output of the vapor device 100 such that data is received by the vapor device 100 from the server, transmitted to the smartphone, and output on a display of the smartphone. In an aspect, data transmitted to the ancillary device can comprise a mixture of vaporizable material and/or instructions to release vapor. For example, the vapor device 100 can be configured to determine a need for the release of vapor into the atmosphere. The vapor device 100 can provide instructions via the network access device 106 to an ancillary device (e.g., another vapor device) to release vapor into the atmosphere.

In an aspect, data can be shared anonymously. The data can be shared over a transient data session with an ancillary device. The transient data session can comprise a session limit. The session limit can be based on one or more of a number of puffs, a time limit, and a total quantity of vaporizable material. The data can comprise usage data and/or a usage profile.

In an aspect, the vapor device 100 can also comprise an input/output device 112 coupled to one or more of the processor 102, the vaporizer 108, the network access device 106, and/or any other electronic component of the vapor device 100. Input can be received from a user or another device and/or output can be provided to a user or another device via the input/output device 112. The input/output device 112 can comprise any combinations of input and/or output devices such as buttons, knobs, keyboards, touch-screens, displays, light-emitting elements, a speaker, and/or the like. In an aspect, the input/output device 112 can comprise an interface port (not shown) such as a wired interface, for example a serial port, a Universal Serial Bus (USB) port, an Ethernet port, or other suitable wired connection. The input/output device 112 can comprise a wireless interface (not shown), for example a transceiver using any suitable wireless protocol, for example WiFi (IEEE 802.11), Bluetooth®, infrared, or other wireless standard. For example, the input/output device 112 can communicate with a smartphone via Bluetooth® such that the inputs and outputs of the smartphone can be used by the user to interface with the vapor device 100. In an aspect, the input/output device 112 can comprise a user interface. The user interface user interface can comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions. In an aspect, regardless of whether the vapor device 100 comprises a display, the vapor device 100 can communicate with an authorized electronic device to provide a user interface via the authorized electronic device that controls functionality of the vapor device 100.

In an aspect, the input/output device 112 can be coupled to an adaptor device to receive power and/or send/receive data signals from an electronic device. For example, the input/output device 112 can be configured to receive power from the adaptor device and provide the power to the power supply 120 to recharge one or more batteries. The input/output device 112 can exchange data signals received from the adaptor device with the processor 102 to cause the processor to execute one or more functions.

In an aspect, the input/output device 112 can comprise a touchscreen interface and/or a biometric interface. For example, the input/output device 112 can include controls that allow the user to interact with and input information and commands to the vapor device 100. For example, with respect to the embodiments described herein, the input/output device 112 can comprise a touch screen display. The input/output device 112 can be configured to provide the content of the exemplary screen shots shown herein, which are presented to the user via the functionality of a display. User inputs to the touch screen display are processed by, for example, the input/output device 112 and/or the processor 102. The input/output device 112 can also be configured to process new content and communications to the system 100. The touch screen display can provide controls and menu selections, and process commands and requests. Application and content objects can be provided by the touch screen display. The input/output device 112 and/or the processor 102 can receive and interpret commands and other inputs, interface with the other components of the vapor device 100 as required. In an aspect, the touch screen display can enable a user to lock, unlock, or partially unlock or lock, the vapor device 100. The vapor device 100 can be transitioned from an idle and locked state into an open state by, for example, moving or dragging an icon on the screen of the vapor device 100, entering in a password/passcode, and the like. The input/output device 112 can thus display information to a user such as a puff count, an amount of vaporizable material remaining in the container 110, battery remaining, signal strength, combinations thereof, and the like.

In an aspect, the input/output device 112 can comprise an audio user interface. A microphone can be configured to receive audio signals and relay the audio signals to the input/output device 112. The audio user interface can be any interface that is responsive to voice or other audio commands. The audio user interface can be configured to cause an action, activate a function, etc, by the vapor device 100 (or another device) based on a received voice (or other audio) command. The audio user interface can be deployed directly on the vapor device 100 and/or via other electronic devices (e.g., electronic communication devices such as a smartphone, a smart watch, a tablet, a laptop, a dedicated audio user interface device, and the like). The audio user interface can be used to control the functionality of the vapor device 100. Such functionality can comprise, but is not limited to, custom mixing of vaporizable material (e.g., eLiquids) and/or ordering custom made eLiquid combinations via an eCommerce service (e.g., specifications of a user's custom flavor mix can be transmitted to an eCommerce service, so that an eLiquid provider can mix a custom eLiquid cartridge for the user). The user can then reorder the custom flavor mix anytime or even send it to friends as a present, all via the audio user interface. The user can also send via voice command a mixing recipe to other users. The other users can utilize the mixing recipe (e.g., via an electronic vapor device having multiple chambers for eLiquid) to sample the same mix via an auto-order to the other users' devices to create the received mixing recipe. A custom mix can be given a title by a user and/or can be defined by parts (e.g., one part liquid A and two parts liquid B). The audio user interface can also be utilized to create and send a custom message to other users, to join eVapor clubs, to receive eVapor chart information, and to conduct a wide range of social networking, location services and eCommerce activities. The audio user interface can be secured via a password (e.g., audio password) which features at least one of tone recognition, other voice quality recognition and, in one aspect, can utilize at least one special cadence as part of the audio password.

The input/output device 112 can be configured to interface with other devices, for example, exercise equipment, computing equipment, communications devices and/or other vapor devices, for example, via a physical or wireless connection. The input/output device 112 can thus exchange data with the other equipment. A user may sync their vapor device 100 to other devices, via programming attributes such as mutual dynamic link library (DLL) 'hooks'. This enables a smooth exchange of data between devices, as can a web interface between devices. The input/output device 112 can be used to upload one or more profiles to the other devices. Using exercise equipment as an example, the one or more profiles can comprise data such as workout routine data (e.g., timing, distance, settings, heart rate, etc. . . . ) and vaping data (e.g., eLiquid mixture recipes, supplements, vaping timing, etc. . . . ). Data from usage of previous exercise sessions can be archived and shared with new electronic vapor devices and/or new exercise equipment so that history and preferences may remain continuous and provide for simplified device settings, default settings, and recommended settings based upon the synthesis of current and archival data.

In an aspect, the vapor device 100 can comprise a vaporizer 108. The vaporizer 108 can be coupled to one or more containers 110. Each of the one or more containers 110 can be configured to hold one or more vaporizable or non-vaporizable materials. The vaporizer 108 can receive the one or more vaporizable or non-vaporizable materials from the one or more containers 110 and heat the one or more vaporizable or non-vaporizable materials until the one or more vaporizable or non-vaporizable materials achieve a vapor state. In various embodiments, instead of heating the one or more vaporizable or non-vaporizable materials, the vaporizer 108 can nebulize or otherwise cause the one or more vaporizable or non-vaporizable materials in the one or more containers 110 to reduce in size into particulates. In various embodiments, the one or more containers 110 can comprise a compressed liquid that can be released to the vaporizer 108 via a valve or another mechanism. In various embodiments, the one or more containers 110 can comprise a wick (not shown) through which the one or more vaporizable or non-vaporizable materials is drawn to the vaporizer 108. The one or more containers 110 can be made of any suitable structural material, such as, an organic polymer, metal, ceramic, composite, or glass material. In an aspect, the vaporizable material can comprise one or more of, a Propylene Glycol (PG) based liquid, a Vegetable Glycerin (VG) based liquid, a water based liquid, combinations thereof, and the like. In an aspect, the vaporizable material can comprise Tetrahydrocannabinol (THC), Cannabidiol (CBD), cannabinol (CBN), combinations thereof, and the like. In a further aspect, the vaporizable material can comprise an extract from *duboisia hopwoodii*.

In an aspect, the vapor device 100 can comprise a mixing element 122. The mixing element 122 can be coupled to the processor 102 to receive one or more control signals. The one or more control signals can instruct the mixing element 122 to withdraw specific amounts of fluid from the one or more containers 110. The mixing element can, in response to a control signal from the processor 102, withdraw select quantities of vaporizable material in order to create a customized mixture of different types of vaporizable material. The liquid withdrawn by the mixing element 122 can be provided to the vaporizer 108.

The vapor device 100 may include a plurality of valves, wherein a respective one of the valves is interposed between the vaporizer 108 and a corresponding one of outlet 114 and/or outlet 124 (e.g., one or more inlets of flexible tubes). Each of the valves may control a flow rate through a respective one of the flexible tubes. For example, each of the plurality of valves may include a lumen of adjustable effective diameter for controlling a rate of vapor flow there through. The assembly may include an actuator, for example a motor, configured to independently adjust respective ones of the valves under control of the processor. The actuator may include a handle or the like to permit manual valve adjustment by the user. The motor or actuator can be coupled to a uniform flange or rotating spindle coupled to the valves and configured for controlling the flow of vapor through each of the valves. Each of the valves can be adjusted so that each of the flexible tubes accommodate the same (equal) rate of vapor flow, or different rates of flow. The processor 102 can be configured to determine settings for the respective ones of the valves each based on at least one of: a selected user preference or an amount of suction applied to a corresponding one of the flexible tubes. A user preference can be determined by the processor 102 based on a user input, which can be electrical or mechanical. An electrical input can be provided, for example, by a touchscreen, keypad, switch, or potentiometer (e.g., the input/output 112). A mechanical input can be provided, for example, by applying suction to a mouthpiece of a tube, turning a valve handle, or moving a gate piece.

The vapor device 100 may further include at least one light-emitting element positioned on or near each of the outlet 114 and/or the outlet 124 (e.g., flexible tubes) and configured to illuminate in response to suction applied to the outlet 114 and/or the outlet 124. At least one of an intensity of illumination or a pattern of alternating between an illuminated state and a non-illuminated state can be adjusted based on an amount of suction. One or more of the at least one light-emitting element, or another light-emitting element, may illuminate based on an amount of vaporizable material available. For example, at least one of an intensity of illumination or a pattern of alternating between an illuminated state and a non-illuminated state can be adjusted based on an amount of the vaporizable material within the vapor device 100. In some aspects, the vapor device 100 may include at least two light-emitting elements positioned on each of the outlet 114 and/or the outlet 124. Each of the at least two light-emitting elements may include a first light-emitting element and an outer light-emitting element positioned nearer the end of the outlet 114 and/or the outlet 124 than the first light-emitting element. Illumination of the at least two light-emitting elements may indicate a direction of a flow of vapor.

In an aspect, input from the input/output device 112 can be used by the processor 102 to cause the vaporizer 108 to vaporize the one or more vaporizable or non-vaporizable materials. For example, a user can depress a button, causing the vaporizer 108 to start vaporizing the one or more vaporizable or non-vaporizable materials. A user can then draw on an outlet 114 to inhale the vapor. In various aspects, the processor 102 can control vapor production and flow to the outlet 114 based on data detected by a flow sensor 116. For example, as a user draws on the outlet 114, the flow sensor 116 can detect the resultant pressure and provide a signal to the processor 102. In response, the processor 102 can cause the vaporizer 108 to begin vaporizing the one or more vaporizable or non-vaporizable materials, terminate vaporizing the one or more vaporizable or non-vaporizable materials, and/or otherwise adjust a rate of vaporization of the one or more vaporizable or non-vaporizable materials. In another aspect, the vapor can exit the vapor device 100 through an outlet 124. The outlet 124 differs from the outlet 114 in that the outlet 124 can be configured to distribute the vapor into the local atmosphere, rather than being inhaled by a user. In an aspect, vapor exiting the outlet 124 can be at least one of aromatic, medicinal, recreational, and/or wellness related. In an aspect, the vapor device 100 can comprise any number of outlets. In an aspect, the outlet 114 and/or the outlet 124 can comprise at least one flexible tube. For example, a lumen of the at least one flexible tube can be in fluid communication with one or more components (e.g., a first container) of the vapor device 100 to provide vapor to a user. In more detailed aspects, the at least one flexible tube may include at least two flexible tubes. Accordingly, the vapor device 100 may further include a second container configured to receive a second vaporizable material such that a first flexible tube can receive vapor from the first vaporizable material and a second flexible tube receive vapor from the second vaporizable material. For example, the at least two flexible tubes can be in fluid communication with the first container and with second container. The vapor device 100 may include an electrical or mechanical sensor configured to sense a pressure level, and therefore suction, in an interior of the flexible tube. Application of suction may activate the vapor device 100 and cause vapor to flow.

In another aspect, the vapor device 100 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid. In an aspect, the vapor device 100 can be configured to permit a user to select between using a heating element of the vaporizer 108 or the piezoelectric dispersing element. In another aspect, the vapor device 100 can be configured to permit a user to utilize both a heating element of the vaporizer 108 and the piezoelectric dispersing element.

In an aspect, the vapor device 100 can comprise a heating casing 126. The heating casing 126 can enclose one or more of the container 110, the vaporizer 108, and/or the outlet 114. In a further aspect, the heating casing 126 can enclose one or more components that make up the container 110, the vaporizer 108, and/or the outlet 114. The heating casing 126 can be made of ceramic, metal, and/or porcelain. The heating casing 126 can have varying thickness. In an aspect, the heating casing 126 can be coupled to the power supply 120 to receive power to heat the heating casing 126. In another aspect, the heating casing 126 can be coupled to the vaporizer 108 to heat the heating casing 126. In another aspect, the heating casing 126 can serve an insulation role.

In an aspect, the vapor device 100 can comprise a filtration element 128. The filtration element 128 can be configured to remove (e.g., filter, purify, etc) contaminants from air entering the vapor device 100. The filtration element 128 can optionally comprise a fan 130 to assist in delivering air to the filtration element 128. The vapor device 100 can be configured to intake air into the filtration element 128, filter the air, and pass the filtered air to the vaporizer 108 for use in vaporizing the one or more vaporizable or non-vaporizable materials. In another aspect, the vapor device 100 can be configured to intake air into the filtration element 128, filter the air, and bypass the vaporizer 108 by passing the filtered air directly to the outlet 114 for inhalation by a user.

In an aspect, the filtration element 128 can comprise cotton, polymer, wool, satin, meta materials and the like. The filtration element 128 can comprise a filter material that at least one airborne particle and/or undesired gas by a mechanical mechanism, an electrical mechanism, and/or a chemical mechanism. The filter material can comprise one or more pieces of a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 128 can comprise electrostatic plates, ultraviolet light, a HEPA filter, combinations thereof, and the like.

In an aspect, the vapor device 100 can comprise a cooling element 132. The cooling element 132 can be configured to cool vapor exiting the vaporizer 108 prior to passing through the outlet 114. The cooling element 132 can cool vapor by utilizing air or space within the vapor device 100. The air used by the cooling element 132 can be either static (existing in the vapor device 100) or drawn into an intake and through the cooling element 132 and the vapor device 100. The intake can comprise various pumping, pressure, fan, or other intake systems for drawing air into the cooling element 132. In an aspect, the cooling element 132 can reside separately or can be integrated the vaporizer 108. The cooling element 132 can be a single cooled electronic element within a tube or space and/or the cooling element 132 can be configured as a series of coils or as a grid like structure. The materials for the cooling element 132 can be metal, liquid, polymer, natural substance, synthetic substance, air, or any combination thereof. The cooling element 132 can be powered by the power supply 120, by a separate battery (not shown), or other power source (not shown) including the use of excess heat energy created by the vaporizer 108 being converted to energy used for cooling by virtue of a small turbine or pressure system to convert the energy. Heat differentials between the vaporizer 108 and the cooling element 132 can also be converted to energy utilizing commonly known geothermal energy principles.

In an aspect, the vapor device 100 can comprise a magnetic element 134. For example, the magnetic element 134 can comprise an electromagnet, a ceramic magnet, a ferrite magnet, and/or the like. The magnetic element 134 can be configured to apply a magnetic field to air as it is brought into the vapor device 100, in the vaporizer 108, and/or as vapor exits the outlet 114.

The input/output device 112 can be used to select whether vapor exiting the outlet 114 should be cooled or not cooled and/or heated or not heated and/or magnetized or not magnetized. For example, a user can use the input/output device 112 to selectively cool vapor at times and not cool vapor at other times. The user can use the input/output device 112 to selectively heat vapor at times and not heat vapor at other times. The user can use the input/output device 112 to selectively magnetize vapor at times and not magnetize vapor at other times. The user can further use the input/output device 112 to select a desired smoothness, temperature, and/or range of temperatures. The user can adjust the temperature of the vapor by selecting or clicking on a clickable setting on a part of the vapor device 100. The user can use, for example, a graphical user interface (GUI) or a mechanical input enabled by virtue of clicking a rotational mechanism at either end of the vapor device 100.

In an aspect, cooling control can be set within the vapor device 100 settings via the processor 102 and system software (e.g., dynamic linked libraries). The memory 104 can store settings. Suggestions and remote settings can be communicated to and/or from the vapor device 100 via the input/output device 112 and/or the network access device 106. Cooling of the vapor can be set and calibrated between heating and cooling mechanisms to what is deemed an ideal temperature by the manufacturer of the vapor device 100 for the vaporizable material. For example, a temperature can be set such that resultant vapor delivers the coolest feeling to the average user but does not present any health risk to the user by virtue of the vapor being too cold, including the potential for rapid expansion of cooled vapor within the lungs and the damaging of tissue by vapor which has been cooled to a temperature which may cause frostbite like symptoms.

In an aspect, the vapor device 100 can be configured to receive air, smoke, vapor or other material and analyze the contents of the air, smoke, vapor or other material using one or more sensors 136 in order to at least one of analyze, classify, compare, validate, refute, and/or catalogue the same. A result of the analysis can be, for example, an identification of at least one of medical, recreational, homeopathic, olfactory elements, spices, other cooking ingredients, ingredients analysis from food products, fuel analysis, pharmaceutical analysis, genetic modification testing analysis, dating, fossil and/or relic analysis and the like. The vapor device 100 can pass utilize, for example, mass spectrometry, PH testing, genetic testing, particle and/or cellular testing, sensor based testing and other diagnostic and wellness testing either via locally available components or by transmitting data to a remote system for analysis.

In an aspect, a user can create a custom scent by using the vapor device 100 to intake air elements, where the vapor device 100 (or third-party networked device) analyzes the olfactory elements and/or biological elements within the sample and then formulates a replica scent within the vapor device 100 (or third-party networked device) that can be accessed by the user instantly, at a later date, with the ability to purchase this custom scent from a networked ecommerce portal.

The vapor device 100 can comprise an intake. The intake can be receptacle for receiving air from an area surrounding the intake. In another aspect, the intake can be a receptacle for receiving at least a portion of a detachable vaporizer. In an aspect, the intake can form an airtight seal with a detachable vaporizer. In another aspect, the intake can form a non-airtight seal with a detachable vaporizer. The vapor device 100 can comprise a pump (or other similar suction mechanism) coupled to the intake. The pump can be configured to draw air from an area surrounding the intake. In an aspect, one or more fan 130 can be configured to assist the pump in drawing air into the vapor device 100.

Air drawn in by the pump through the intake 138 can be passed to an analysis chamber. The analysis chamber can be a receptacle within the vapor device 100 configured for holding the drawn air and for exposing the air to one or more sensors 136 in order to at least one of analyze, classify, compare, validate, refute, and/or catalogue the same. A result of the analysis can be, for example, a performance indicator for a detachable vaporizer (any measure indicative of whether a detachable vaporizer is performing as expected), an identification of at least one of medical, recreational, homeopathic, olfactory elements, spices, other cooking ingredients, ingredients analysis from food products, fuel analysis, pharmaceutical analysis, and the like. The vapor device 100 can utilize, for example, mass spectrometry, gas chromatography, PH testing, particle and/or cellular testing, sensor based testing and other diagnostic and wellness testing either via locally available components or by transmitting data to a remote system for analysis. The mass spectrometry and/or gas chromatography systems disclosed herein can be implemented in a compact form factor, as is known in the art. Mass spectrometry is an analytical chemistry technique that identifies an amount and type of chemicals present in a sample by measuring the mass-to-charge ratio and abundance of gas-phase ions. A mass spectrum (plural spectra) is a plot of the ion signal as a function of the mass-to-charge ratio. The spectra are used to determine the elemental or isotopic signature of a sample, the masses of particles and of molecules, and to elucidate the chemical structures of molecules, such as peptides and other chemical compounds. Mass spectrometry works by ionizing chemical compounds to generate charged molecules or molecule fragments and measuring their mass-to-charge ratios.

In a typical mass spectrometry procedure, a sample of the drawn air, is ionized, for example by bombarding the air/vapor with electrons. This can cause some of the sample's molecules to break into charged fragments. These ions are then separated according to their mass-to-charge ratio, typically by accelerating them and subjecting them to an electric or magnetic field: ions of the same mass-to-charge ratio will undergo the same amount of deflection. The ions are detected by a mechanism capable of detecting charged particles, such as an electron multiplier. Results are displayed as spectra of the relative abundance of detected ions as a function of the mass-to-charge ratio. The atoms or molecules in the sample can be identified by correlating known masses to the identified masses stored on the memory device 104 or through a characteristic fragmentation pattern. Thus, a composition of the drawn air can be determined.

In another aspect, nanosensor technology using nanostructures: single walled carbon nanotubes (SWNTs), combined with a silicon-based microfabrication and micromachining process can be used. This technology provides a sensor array that can accommodate different nanostructures for specific applications with the advantages of high sensitivity, low power consumption, compactness, high yield and low cost. This platform provides an array of sensing elements for chemical detection. Each sensor in the array can comprise a nanostructure—chosen from many different categories of sensing material—and an interdigitated electrode (IDE) as a transducer. It is one type of electrochemical sensor that implies the transfer of charge from one electrode to another. This means that at least two electrodes constitute an electrochemical cell to form a closed electrical circuit. Due to the interaction between nanotube devices and gas molecules, the electron configuration is changed in the nanostructured sensing device, therefore, the changes in the electronic signal such as current or voltage were observed before and during the exposure of gas species (such as NO 2, NH 3, etc.). By measuring the conductivity change of the CNT device, the concentration of the chemical species, such as gas molecules in the air/vapor drawn from the vapor device 100, can be measured.

In another aspect, the one or more sensors 136 can be configured to sense negative environmental conditions (e.g., adverse weather, smoke, fire, chemicals (e.g., such as $CO_2$ or formaldehyde), adverse pollution, and/or disease outbreaks, and the like). The one or more sensors 136 can comprise one or more of, a biochemical/chemical sensor, a thermal sensor, a radiation sensor, a mechanical sensor, an optical sensor, a mechanical sensor, a magnetic sensor, an electrical sensor, combinations thereof and the like. The biochemical/chemical sensor can be configured to detect one or more biochemical/chemicals causing a negative environmental condition such as, but not limited to, smoke, a vapor, a gas, a liquid, a solid, an odor, combinations thereof, and/or the like. The biochemical/chemical sensor can comprise one or more of a mass spectrometer, a conducting/nonconducting regions sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, a electrochemical cell, a conducting polymer sensor, a catalytic gas sensor, an organic semiconducting gas sensor, a solid electrolyte gas sensors, a piezoelectric quartz crystal sensor, and/or combinations thereof.

A semiconductor sensor can be configured to detect gases by a chemical reaction that takes place when the gas comes in direct contact with the sensor. Tin dioxide is the most common material used in semiconductor sensors, and the electrical resistance in the sensor is decreased when it comes in contact with the monitored gas. The resistance of the tin dioxide is typically around 50 k$\Omega$ in air but can drop to around 3.5 k$\Omega$ in the presence of 1% methane. This change in resistance is used to calculate the gas concentration. Semiconductor sensors can be commonly used to detect hydrogen, oxygen, alcohol vapor, and harmful gases such as carbon monoxide. A semiconductor sensors can be used as a carbon monoxide sensors. A semiconductor sensor can be used as a breathalyzers. Because the sensor must come in contact with the gas to detect it, semiconductor sensors work over a smaller distance than infrared point or ultrasonic detectors.

The thermal sensor can be configured to detect temperature, heat, heat flow, entropy, heat capacity, combinations thereof, and the like. Exemplary thermal sensors include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

The radiation sensor can be configured to detect gamma rays, X-rays, ultra-violet rays, visible, infrared, microwaves and radio waves. Exemplary radiation sensors include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors.

The optical sensor can be configured to detect visible, near infrared, and infrared waves. The mechanical sensor can be configured to detect displacement, velocity, acceleration, force, torque, pressure, mass, flow, acoustic wavelength, and amplitude. Exemplary mechanical sensors include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors. The magnetic sensor can be configured to detect magnetic field, flux, magnetic moment, magnetization, and magnetic permeability. The electrical sensor can be configured to detect charge, current, voltage, resistance, conductance, capacitance, inductance, dielectric permittivity, polarization and frequency.

Upon sensing a negative environmental condition, the one or more sensors 122 can provide data to the processor 102 to determine the nature of the negative environmental condition and to generate/transmit one or more alerts based on the negative environmental condition. The one or more alerts can be deployed to the vapor device 100 user's wireless device and/or synced accounts. For example, the network device access device 106 can be used to transmit the one or more alerts directly (e.g., via Bluetooth®) to a user's smartphone to provide information to the user. In another aspect, the network access device 106 can be used to transmit sensed information and/or the one or more alerts to a remote server for use in syncing one or more other devices used by the user (e.g., other vapor devices, other electronic devices (smartphones, tablets, laptops, etc. . . . ). In another aspect, the one or more alerts can be provided to the user of the vapor device 100 via vibrations, audio, colors, and the like deployed from the mask, for example through the input/output device 112. For example, the input/output device 112 can comprise a small vibrating motor to alert the user to one or more sensed conditions via tactile sensation. In another example, the input/output device 112 can comprise one or more LED's of various colors to provide visual information to the user. In another example, the input/output device 112 can comprise one or more speakers that can provide audio information to the user. For example, various patterns of beeps, sounds, and/or voice recordings can be utilized to provide the audio information to the user. In another example, the input/output device 112 can comprise an LCD screen/touchscreen that provides a summary and/or detailed information regarding the negative environmental condition and/or the one or more alerts.

In another aspect, upon sensing a negative environmental condition, the one or more sensors 136 can provide data to the processor 102 to determine the nature of the negative environmental condition and to provide a recommendation for mitigating and/or to actively mitigate the negative environmental condition. Mitigating the negative environmental conditions can comprise, for example, applying a filtration system, a fan, a fire suppression system, engaging a HVAC system, and/or one or more vaporizable and/or non-vaporizable materials. The processor 102 can access a database stored in the memory device 104 to make such a determination or the network device 106 can be used to request information from a server to verify the sensor findings. In an aspect, the server can provide an analysis service to the vapor device 100. For example, the server can analyze data sent by the vapor device 100 based on a reading from the one or more sensors 136. The server can determine and transmit one or more recommendations to the vapor device 100 to mitigate the sensed negative environmental condition. The vapor device 100 can use the one or more recommendations to activate a filtration system, a fan, a fire suppression system engaging a HVAC system, and/or to vaporize one or more vaporizable or non-vaporizable materials to assist in countering effects from the negative environmental condition.

In an aspect, the vapor device 100 can comprise a global positioning system (GPS) unit 118. The GPS 118 can detect a current location of the device 100. In some aspects, a user can request access to one or more services that rely on a current location of the user. For example, the processor 102 can receive location data from the GPS 118, convert it to usable data, and transmit the usable data to the one or more services via the network access device 106. GPS unit 118 can receive position information from a constellation of satellites operated by the U.S. Department of Defense. Alternately, the GPS unit 118 can be a GLONASS receiver operated by the Russian Federation Ministry of Defense, or any other positioning device capable of providing accurate location information (for example, LORAN, inertial navigation, and the like). The GPS unit 118 can contain additional logic, either software, hardware or both to receive the Wide Area Augmentation System (WAAS) signals, operated by the Federal Aviation Administration, to correct dithering errors and provide the most accurate location possible. Overall accuracy of the positioning equipment subsystem containing WAAS is generally in the two meter range.

Figure 2:
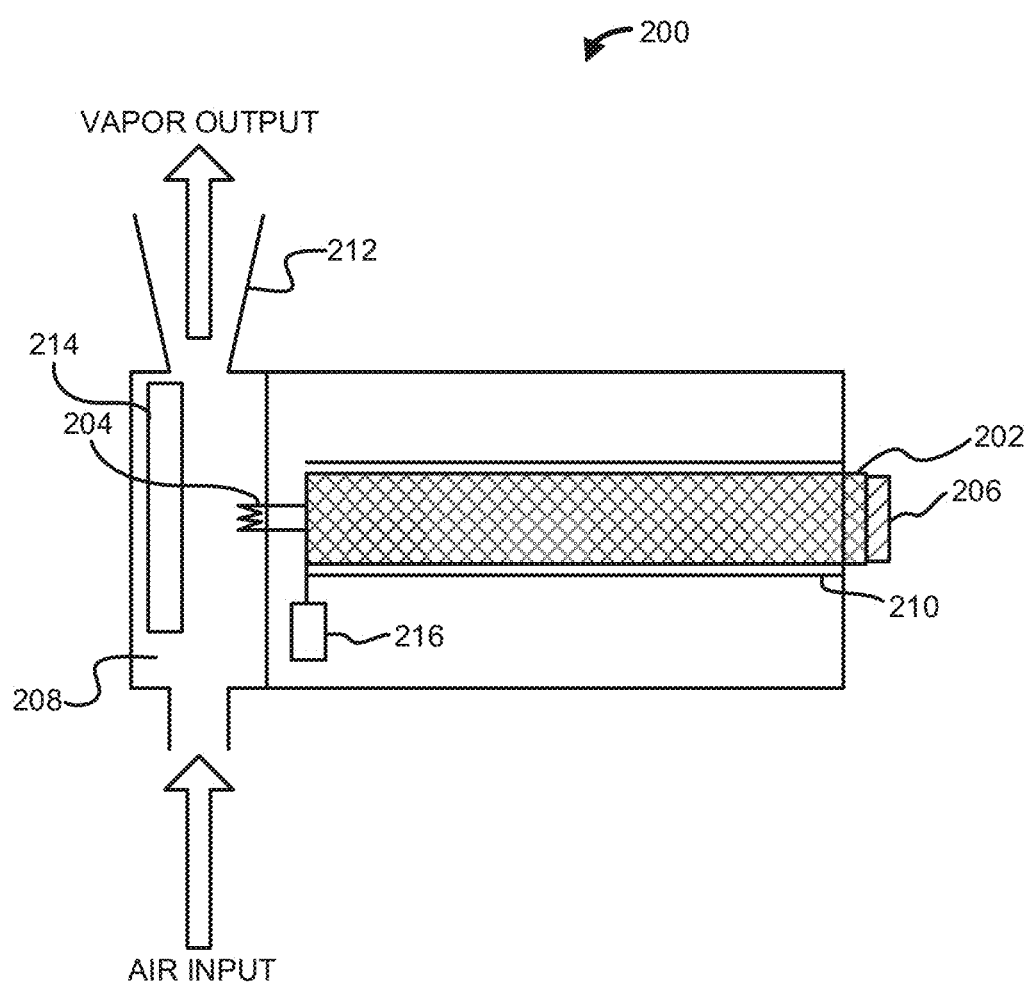
FIG. 2 illustrates an exemplary vaporizer.

FIG. 2 illustrates an exemplary vaporizer 200. The vaporizer 200 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vaporizer 200 can be used internally of the vapor device 100 or can be a separate device. For example, the vaporizer 200 can be used in place of the vaporizer 108.

The vaporizer 200 can comprise or be coupled to one or more containers 202 containing a vaporizable material, for example a fluid. For example, coupling between the vaporizer 200 and the one or more containers 202 can be via a wick 204, via a valve, or by some other structure. Coupling can operate independently of gravity, such as by capillary action or pressure drop through a valve. The vaporizer 200 can be configured to vaporize the vaporizable material from the one or more containers 202 at controlled rates in response to mechanical input from a component of the vapor device 100, and/or in response to control signals from the processor 102 or another component. Vaporizable material (e.g., fluid) can be supplied by one or more replaceable cartridges 206. In an aspect the vaporizable material can comprise aromatic elements. In an aspect, the aromatic elements can be medicinal, recreational, and/or wellness related. The aromatic element can include, but is not limited to, at least one of lavender or other floral aromatic eLiquids, mint, menthol, herbal soil or geologic, plant based, name brand perfumes, custom mixed perfume formulated inside the vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . . . ). The one or more replaceable cartridges 206 can contain the vaporizable material. If the vaporizable material is liquid, the cartridge can comprise the wick 204 to aid in transporting the liquid to a mixing chamber 208. In the alternative, some other transport mode can be used. Each of the one or more replaceable cartridges 206 can be configured to fit inside and engage removably with a receptacle (such as the container 202 and/or a secondary container) of the vapor device 100. In an alternative, or in addition, one or more fluid containers 210 can be fixed in the vapor device 100 and configured to be refillable. In an aspect, one or more materials can be vaporized at a single time by the vaporizer 200. For example, some material can be vaporized and drawn through an exhaust port 212 and/or some material can be vaporized and exhausted via a smoke simulator outlet (not shown).

The mixing chamber 208 can also receive an amount of one or more compounds (e.g., vaporizable material) to be vaporized. For example, the processor 102 can determine a first amount of a first compound and determine a second amount of a second compound. The processor 102 can cause the withdrawal of the first amount of the first compound from a first container into the mixing chamber and the second amount of the second compound from a second container into the mixing chamber. The processor 102 can also determine a target dose of the first compound, determine a vaporization ratio of the first compound and the second compound based on the target dose, determine the first amount of the first compound based on the vaporization ratio, determine the second amount of the second compound based on the vaporization ratio, and cause the withdrawal of the first amount of the first compound into the mixing chamber, and the withdrawal of the second amount of the second compound into the mixing chamber.

The processor 102 can also determine a target dose of the first compound, determine a vaporization ratio of the first compound and the second compound based on the target dose, determine the first amount of the first compound based on the vaporization ratio, and determine the second amount of the second compound based on the vaporization ratio. After expelling the vapor through an exhaust port for inhalation by a user, the processor 102 can determine that a cumulative dose is approaching the target dose and reduce the vaporization ratio. In an aspect, one or more of the vaporization ratio, the target dose, and/or the cumulative dose can be determined remotely and transmitted to the vapor device 100 for use.

In operation, a heating element 214 can vaporize or nebulize the vaporizable material in the mixing chamber 208, producing an inhalable vapor/mist that can be expelled via the exhaust port 212. In an aspect, the heating element 214 can comprise a heater coupled to the wick (or a heated wick) 204 operatively coupled to (for example, in fluid communication with) the mixing chamber 210. The heating element 214 can comprise a nickel-chromium wire or the like, with a temperature sensor (not shown) such as a thermistor or thermocouple. Within definable limits, by controlling power to the wick 204, a rate of vaporization can be independently controlled. A multiplexer 216 can receive power from any suitable source and exchange data signals with a processor, for example, the processor 102 of the vapor device 100, for control of the vaporizer 200. At a minimum, control can be provided between no power (off state) and one or more powered states. Other control mechanisms can also be suitable.

In another aspect, the vaporizer 200 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In an aspect, the vaporizer 200 can be configured to permit a user to select between using the heating element 214 or the piezoelectric dispersing element. In another aspect, the vaporizer 200 can be configured to permit a user to utilize both the heating element 214 and the piezoelectric dispersing element.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid.

Figure 3:
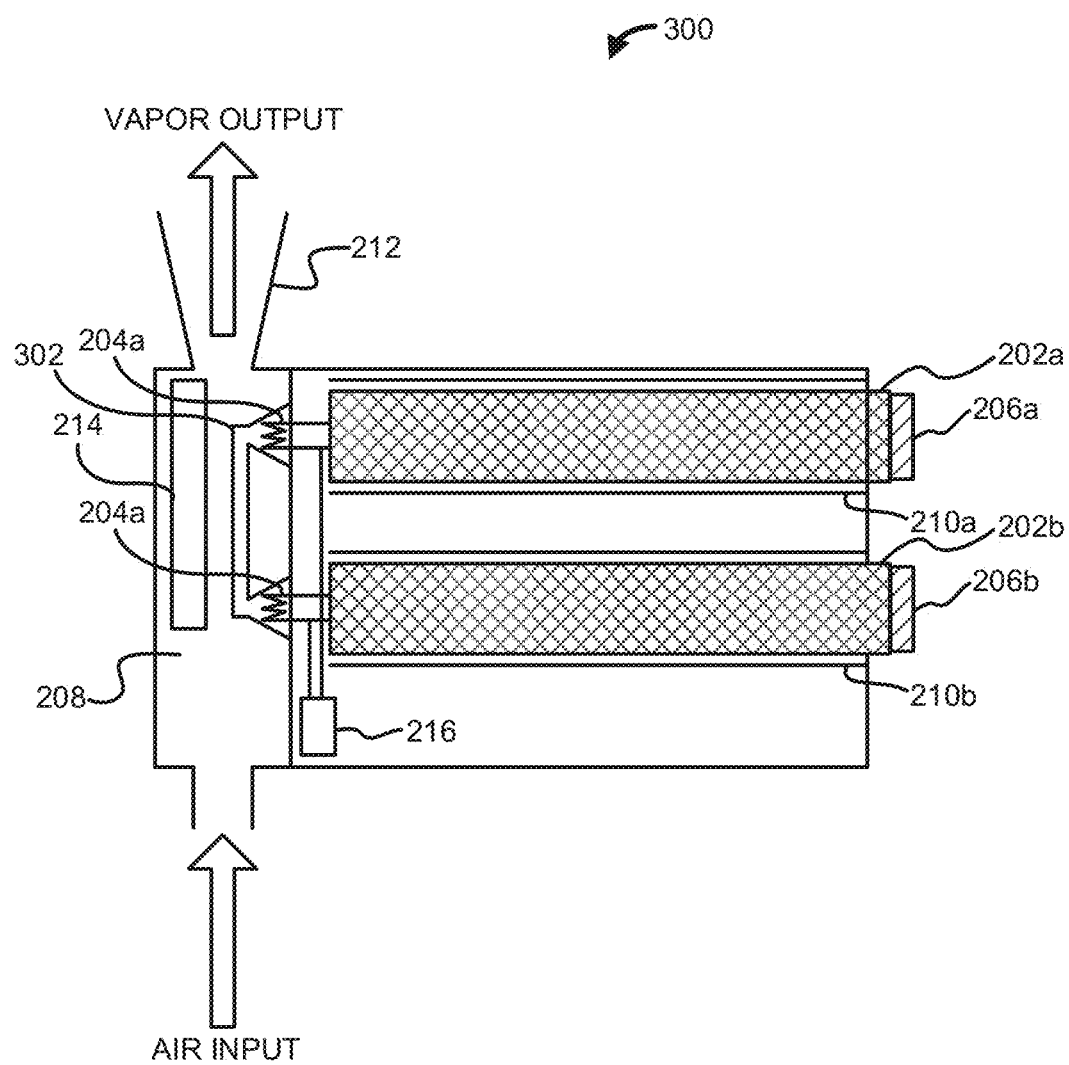
FIG. 3 illustrates an exemplary vaporizer configured for vaporizing a mixture of vaporizable material.
Figure 4:
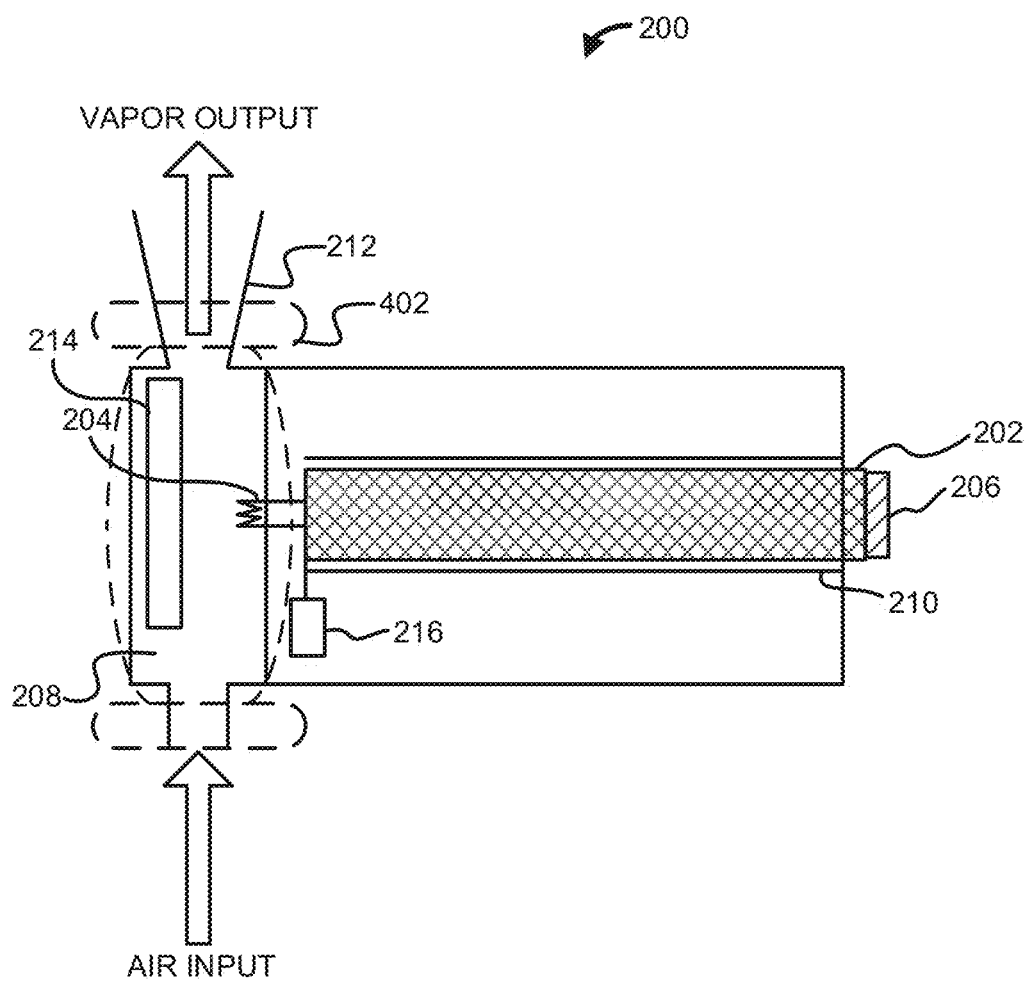
FIG. 4 illustrates an exemplary vaporizer device configured for smooth vapor delivery.
Figure 5:
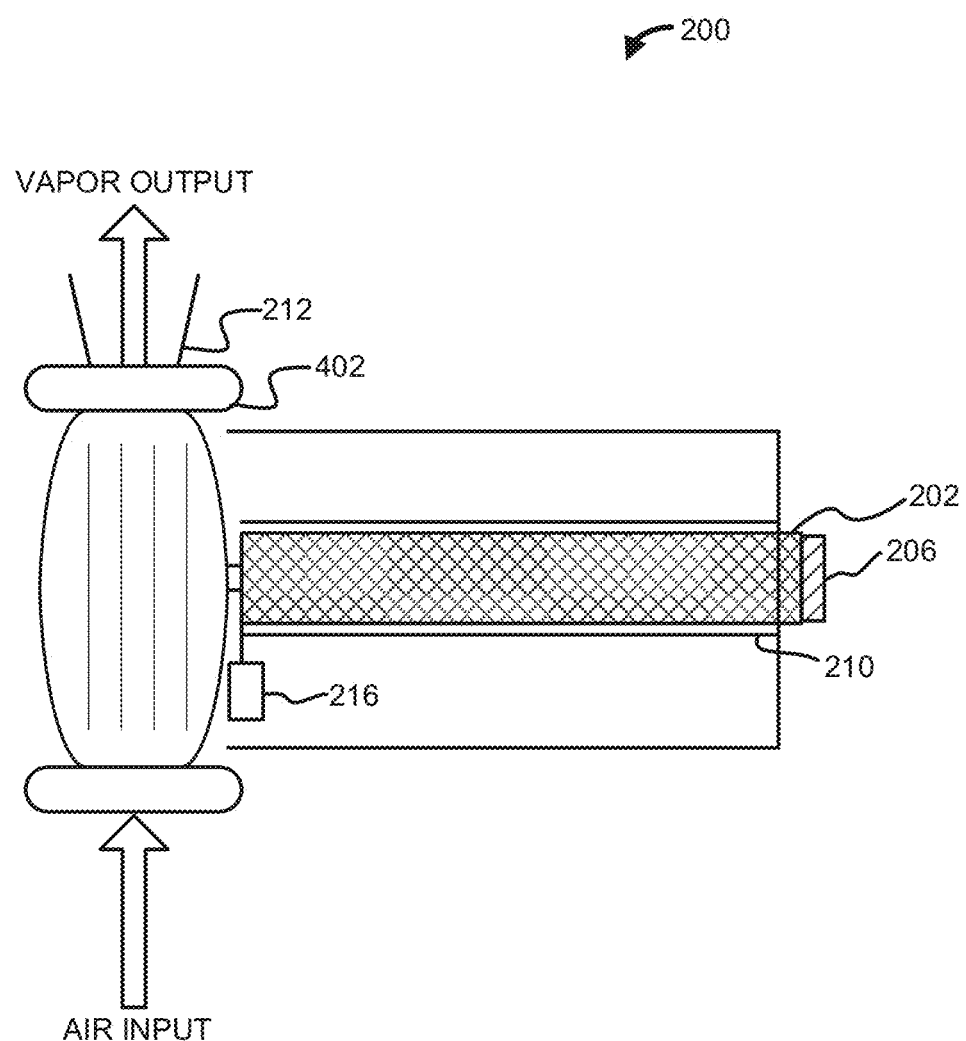
FIG. 5 illustrates another exemplary vaporizer configured for smooth vapor delivery.
Figure 6:
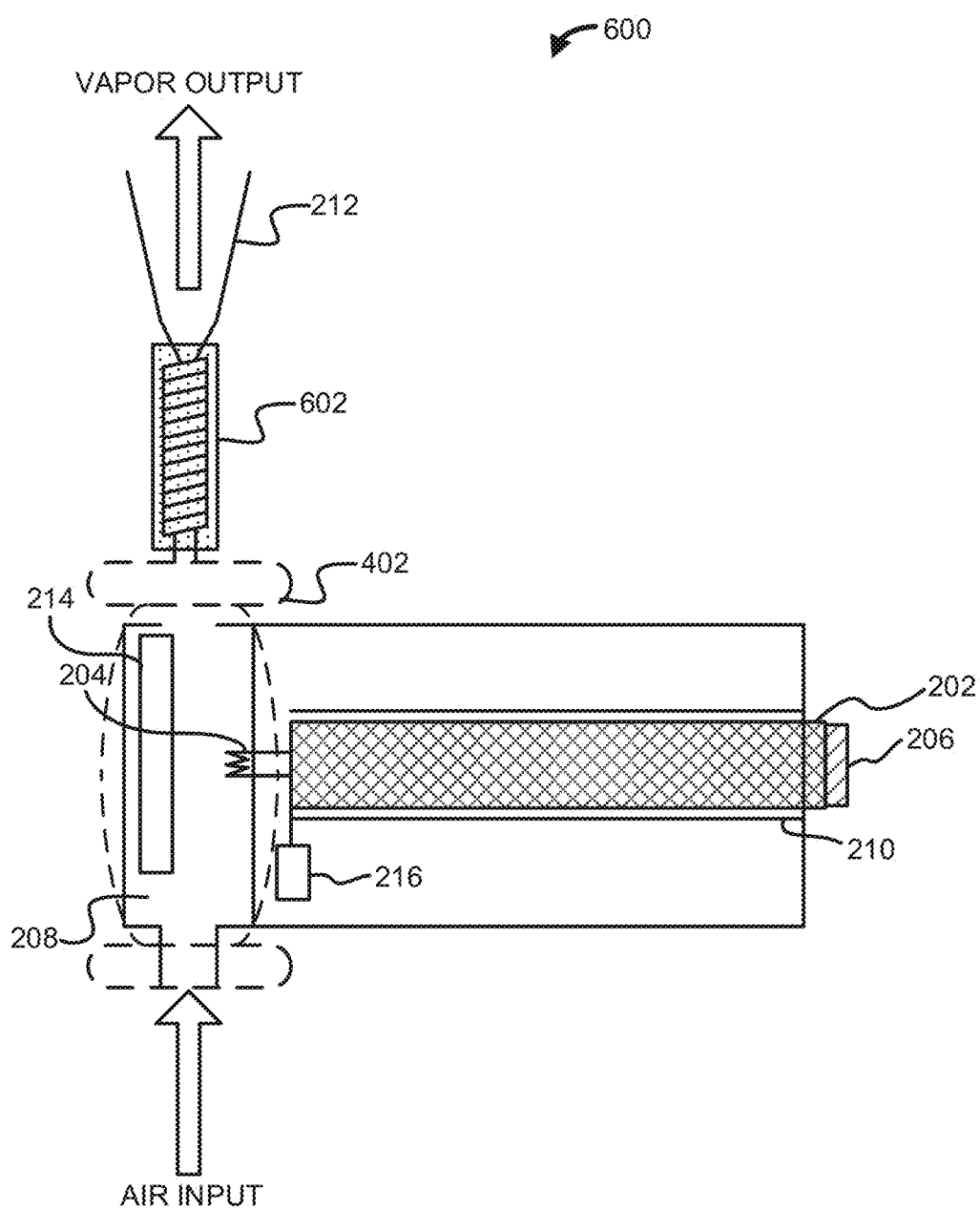
FIG. 6 illustrates another exemplary vaporizer configured for smooth vapor delivery.

FIG. 3 illustrates a vaporizer 300 that comprises the elements of the vaporizer 200 with two containers 202*a* and 202*b* containing a vaporizable material, for example a fluid or a solid. In an aspect, the fluid can be the same fluid in both containers or the fluid can be different in each container. In an aspect the fluid can comprise aromatic elements. The aromatic element can include, but is not limited to, at least one of lavender or other floral aromatic eLiquids, mint, menthol, herbal soil or geologic, plant based, name brand perfumes, custom mixed perfume formulated inside the vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . . . ). Coupling between the vaporizer 200 and the container 202*a* and the container 202*b* can be via a wick 204*a* and a wick 204*b*, respectively, via a valve, or by some other structure. Coupling can operate independently of gravity, such as by capillary action or pressure drop through a valve. The vaporizer 300 can be configured to mix in varying proportions the fluids contained in the container 202*a* and the container 202*b* and vaporize the mixture at controlled rates in response to mechanical input from a component of the vapor device 100, and/or in response to control signals from the processor 102 or another component. For example, based on a vaporization ratio. In an aspect, a mixing element 302 can be coupled to the container 202*a* and the container 202*b*. The mixing element can, in response to a control signal from the processor 102, withdraw select quantities of vaporizable material in order to create a customized mixture of different types of vaporizable material. Vaporizable material (e.g., fluid) can be supplied by one or more replaceable cartridges 206*a* and 206*b*. The one or more replaceable cartridges 206*a* and 206*b* can contain a vaporizable material. If the vaporizable material is liquid, the cartridge can comprise the wick 204*a* or 204*b* to aid in transporting the liquid to a mixing chamber 208. In the alternative, some other transport mode can be used. Each of the one or more replaceable cartridges 206*a* and 206*b* can be configured to fit inside and engage removably with a receptacle (such as the container 202*a* or the container 202*b* and/or a secondary container) of the vapor device 100. In an alternative, or in addition, one or more fluid containers 210*a* and 210*b* can be fixed in the vapor device 100 and configured to be refillable. In an aspect, one or more materials can be vaporized at a single time by the vaporizer 300. For example, some material can be vaporized and drawn through an exhaust port 212 and/or some material can be vaporized and exhausted via a smoke simulator outlet (not shown).

FIG. 4 illustrates a vaporizer 200 that comprises the elements of the vaporizer 200 with a heating casing 402. The heating casing 402 can enclose the heating element 214 or can be adjacent to the heating element 214. The heating casing 402 is illustrated with dashed lines, indicating components contained therein. The heating casing 402 can be made of ceramic, metal, and/or porcelain. The heating casing 402 can have varying thickness. In an aspect, the heating casing 402 can be coupled to the multiplexer 216 to receive power to heat the heating casing 402. In another aspect, the heating casing 402 can be coupled to the heating element 214 to heat the heating casing 402. In another aspect, the heating casing 402 can serve an insulation role.

FIG. 5 illustrates the vaporizer 200 of FIG. 2 and FIG. 4, but illustrates the heating casing 402 with solid lines, indicating components contained therein. Other placements of the heating casing 402 are contemplated. For example, the heating casing 402 can be placed after the heating element 214 and/or the mixing chamber 208.

FIG. 6 illustrates a vaporizer 600 that comprises the elements of the vaporizer 200 of FIG. 2 and FIG. 4, with the addition of a cooling element 602. The vaporizer 600 can optionally comprise the heating casing 402. The cooling element 602 can comprise one or more of a powered cooling element, a cooling air system, and/or or a cooling fluid system. The cooling element 602 can be self-powered, co-powered, or directly powered by a battery and/or charging system within the vapor device 100 (e.g., the power supply 120). In an aspect, the cooling element 602 can comprise an electrically connected conductive coil, grating, and/or other design to efficiently distribute cooling to the at least one of the vaporized and/or non-vaporized air. For example, the cooling element 602 can be configured to cool air as it is brought into the vaporizer 600/mixing chamber 208 and/or to cool vapor after it exits the mixing chamber 208. The cooling element 602 can be deployed such that the cooling element 602 is surrounded by the heated casing 402 and/or the heating element 214. In another aspect, the heated casing 402 and/or the heating element 214 can be surrounded by the cooling element 602. The cooling element 602 can utilize at least one of cooled air, cooled liquid, and/or cooled matter.

In an aspect, the cooling element 602 can be a coil of any suitable length and can reside proximate to the inhalation point of the vapor (e.g., the exhaust port 212). The temperature of the air is reduced as it travels through the cooling element 602. In an aspect, the cooling element 602 can comprise any structure that accomplishes a cooling effect. For example, the cooling element 602 can be replaced with a screen with a mesh or grid-like structure, a conical structure, and/or a series of cooling airlocks, either stationary or opening, in a periscopic/telescopic manner. The cooling element 602 can be any shape and/or can take multiple forms capable of cooling heated air, which passes through its space.

In an aspect, the cooling element 602 can be any suitable cooling system for use in a vapor device. For example, a fan, a heat sink, a liquid cooling system, a chemical cooling system, combinations thereof, and the like. In an aspect, the cooling element 602 can comprise a liquid cooling system whereby a fluid (e.g., water) passes through pipes in the vaporizer 600. As this fluid passes around the cooling element 602, the fluid absorbs heat, cooling air in the cooling element 602. After the fluid absorbs the heat, the fluid can pass through a heat exchanger which transfers the heat from the fluid to air blowing through the heat exchanger. By way of further example, the cooling element 602 can comprise a chemical cooling system that utilizes an endothermic reaction. An example of an endothermic reaction is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus, the vaporizer 600 can comprise a chamber for receiving the cooling element 602 in the form of a "cold pack." The cold pack can be activated prior to insertion into the vaporizer 600 or can be activated after insertion through use of a button/switch and the like to mechanically activate the cold pack inside the vaporizer 400.

In an aspect, the cooling element 602 can be selectively moved within the vaporizer 600 to control the temperature of the air mixing with vapor. For example, the cooling element 602 can be moved closer to the exhaust port 212 or further from the exhaust port 212 to regulate temperature. In another aspect, insulation can be incorporated as needed to maintain the integrity of heating and cooling, as well as absorbing any unwanted condensation due to internal or external conditions, or a combination thereof. The insulation can also be selectively moved within the vaporizer 600 to control the temperature of the air mixing with vapor. For example, the insulation can be moved to cover a portion, none, or all of the cooling element 602 to regulate temperature.

Figure 7:
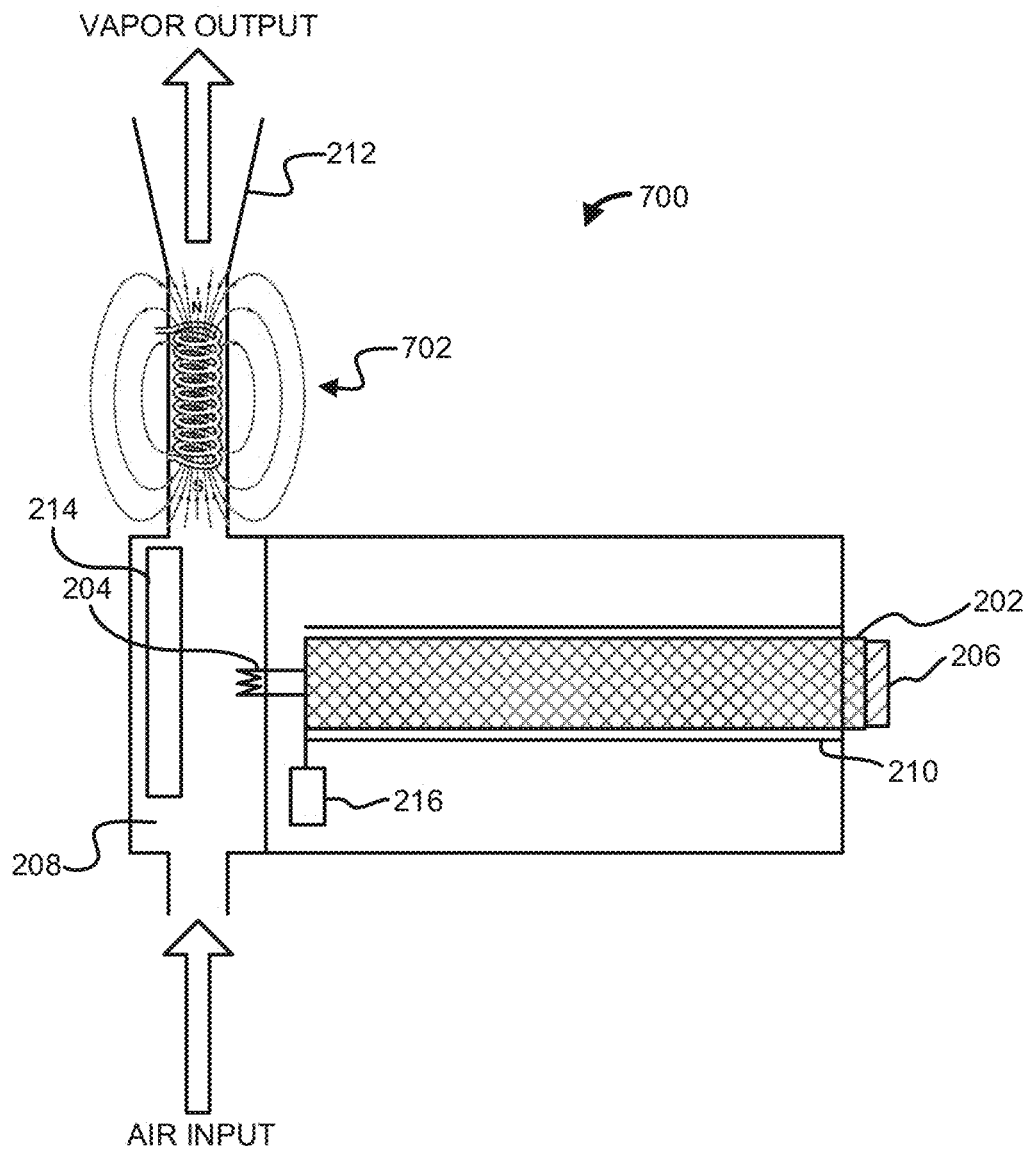
FIG. 7 illustrates another exemplary vaporizer configured for smooth vapor delivery.

FIG. 7 illustrates a vaporizer 700 that comprises elements in common with the vaporizer 200. The vaporizer 700 can optionally comprise the heating casing 402 (not shown) and/or the cooling element 602 (not shown). The vaporizer 700 can comprise a magnetic element 702. The magnetic element 702 can apply a magnetic field to vapor after exiting the mixing chamber 208. The magnetic field can cause positively and negatively charged particles in the vapor to curve in opposite directions, according to the Lorentz force law with two particles of opposite charge. The magnetic field can be created by at least one of an electric current generating a charge or a pre-charged magnetic material deployed within the vapor device 100. In an aspect, the magnetic element 702 can be built into the mixing chamber 208, the cooling element 602, the heating casing 402, or can be a separate magnetic element 702.

Figure 8:
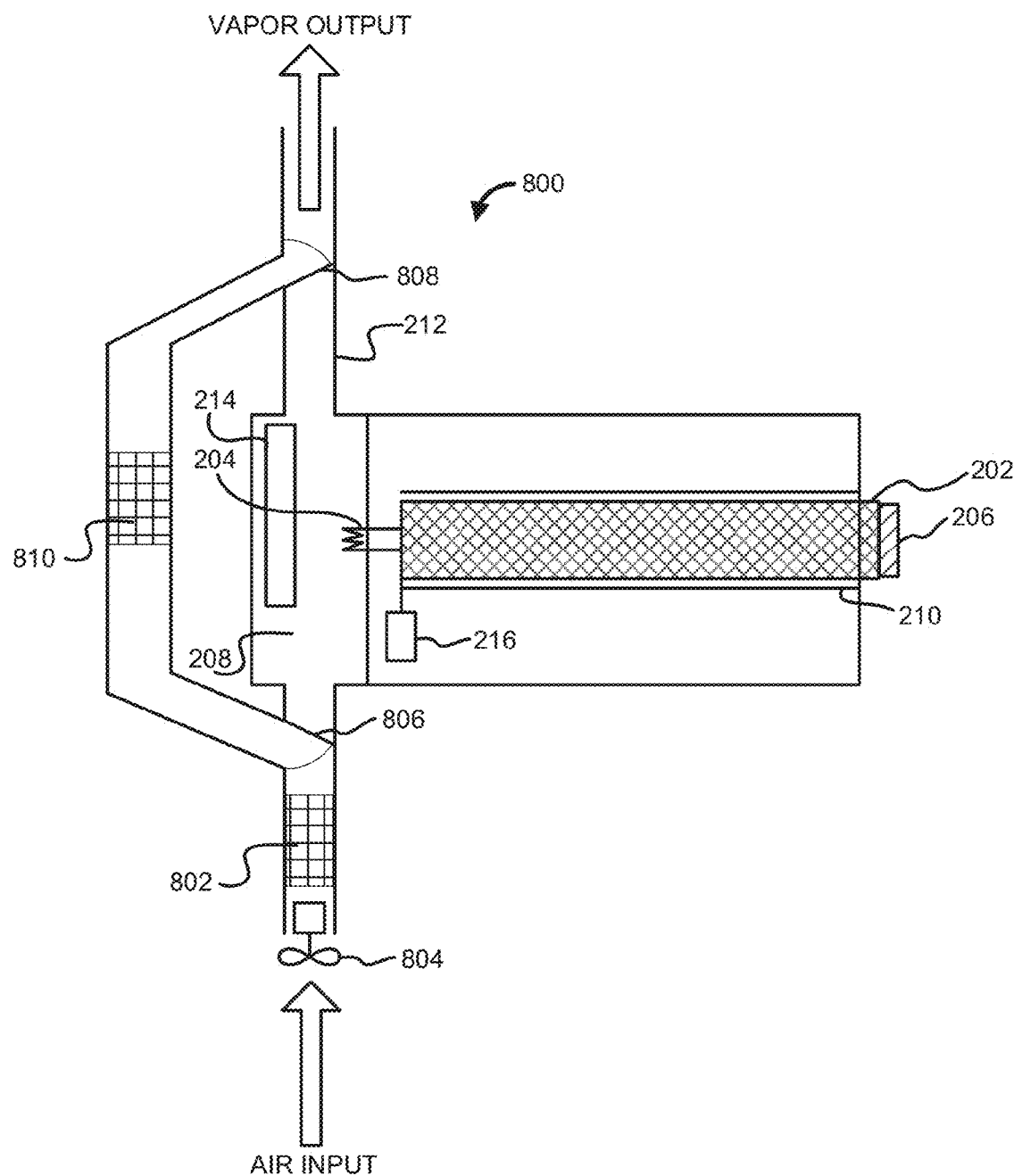
FIG. 8 illustrates an exemplary vaporizer configured for filtering air.

FIG. 8 illustrates a vaporizer 800 that comprises elements in common with the vaporizer 200. In an aspect, the vaporizer 800 can comprise a filtration element 802. The filtration element 802 can be configured to remove (e.g., filter, purify, etc) contaminants from air entering the vaporizer 800. The filtration element 802 can optionally comprise a fan 804 to assist in delivering air to the filtration element 802. The vaporizer 800 can be configured to intake air into the filtration element 802, filter the air, and pass the filtered air to the mixing chamber 208 for use in vaporizing the one or more vaporizable or non-vaporizable materials. In another aspect, the vaporizer 800 can be configured to intake air into the filtration element 802, filter the air, and bypass the mixing chamber 208 by engaging a door 806 and a door 808 to pass the filtered air directly to the exhaust port 212 for inhalation by a user. In an aspect, filtered air that bypasses the mixing chamber 208 by engaging the door 806 and the door 808 can pass through a second filtration element 810 to further remove (e.g., filter, purify, etc) contaminants from air entering the vaporizer 800. In an aspect, the vaporizer 800 can be configured to deploy and/or mix a proper/safe amount of oxygen which can be delivered either via the one or more replaceable cartridges 206 or via air pumped into a mask from external air and filtered through the filtration element 802 and/or the filtration element 810.

In an aspect, the filtration element 802 and/or the filtration element 810 can comprise cotton, polymer, wool, satin, meta materials and the like. The filtration element 802 and/or the filtration element 810 can comprise a filter material that at least one airborne particle and/or undesired gas by a mechanical mechanism, an electrical mechanism, and/or a chemical mechanism. The filter material can comprise one or more pieces of, a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 802 and/or the filtration element 810 can comprise electrostatic plates, ultraviolet light, a HEPA filter, combinations thereof, and the like.

Figure 9:
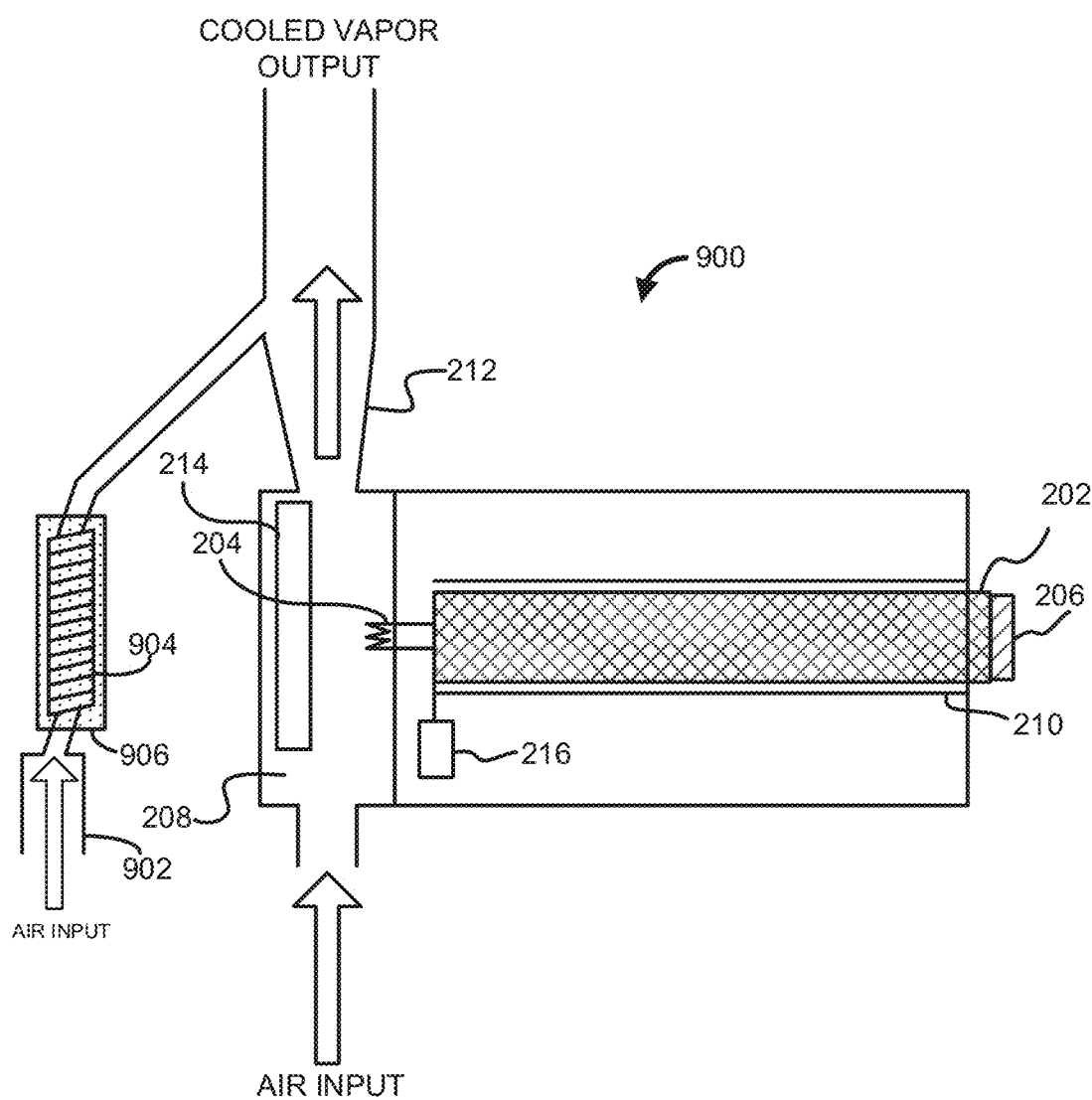
FIG. 9 illustrates another exemplary vaporizer configured for smooth vapor delivery.

FIG. 9 illustrates an exemplary vaporizer 900. The vaporizer 900 comprises elements in common with the vaporizer 200. In an aspect, the vapor expelled via the exhaust port 212 can be cooled by introduction of cooler air prior to inhalation by a user. Air can be drawn into the vaporizer 900 via an intake port 902. The intake port 902 can be the same intake port used to provide air input to the mixing chamber 208 or can be separate and distinct intake port. Air received in to the intake port 902 can be passed through a coil 904. The coil 904 can be of any suitable length and can reside proximate to the inhalation point of the vapor (e.g., the exhaust port 212). The temperature of the air is reduced as it travels through the coil 904. In an aspect, the coil 904 can comprise any structure that accomplishes a cooling effect. For example, the coil 904 can be replaced with a screen with a mesh or grid-like structure, a conical structure, and/or a series of cooling airlocks, either stationary or opening, in a periscopic/telescopic manner. The coil 904 can be any shape and/or can take multiple forms capable of cooling heated air, which passes through its space.

In an aspect, the coil 904 can be cooled by a cooling element 906. In an aspect, the coil 904 and the cooling element 906 can be combined into a single cooling element. Accordingly, the temperature of air is reduced as it travels through the coil 904 prior to mixing with vapor that is exiting the mixing chamber 208. In an aspect, the cooling element 906 can be any suitable cooling system for use in a vapor device. For example, a fan, a heat sink, a liquid cooling system, a chemical cooling system, combinations thereof, and the like. In an aspect, the cooling element 906 can comprise a liquid cooling system whereby a fluid (e.g., water) passes through pipes in the vaporizer 900. As this fluid passes around the coil 904, the fluid absorbs heat, cooling air in the coil 904. After the fluid absorbs the heat, the fluid can pass through a heat exchanger which transfers the heat from the fluid to air blowing through the heat exchanger. By way of further example, the cooling element 906 can comprise a chemical cooling system that utilizes an endothermic reaction. An example of an endothermic reaction is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus, the vaporizer 900 can comprise a chamber for receiving the cooling element 906 in the form of a "cold pack." The cold pack can be activated prior to insertion into the vaporizer 900 or can be activated after insertion through use of a button/switch and the like to mechanically activate the cold pack inside the vaporizer 900.

In an aspect, the cooling element 906 and the coil 904 can be selectively moved within the vaporizer 900 to control the temperature of the air mixing with vapor. For example, the cooling element 906 and the coil 904 can be moved closer to the exhaust port 212 or further from the exhaust port 212 to regulate temperature. In another aspect, insulation can be incorporated as needed to maintain the integrity of heating and cooling, as well as absorbing any unwanted condensation due to internal or external conditions, or a combination thereof. The insulation can also be selectively moved within the vaporizer 900 to control the temperature of the air mixing with vapor. For example, the insulation can be moved to cover a portion, none, or all of the cooling element 906 and the coil 904 to regulate temperature.

Figure 10:
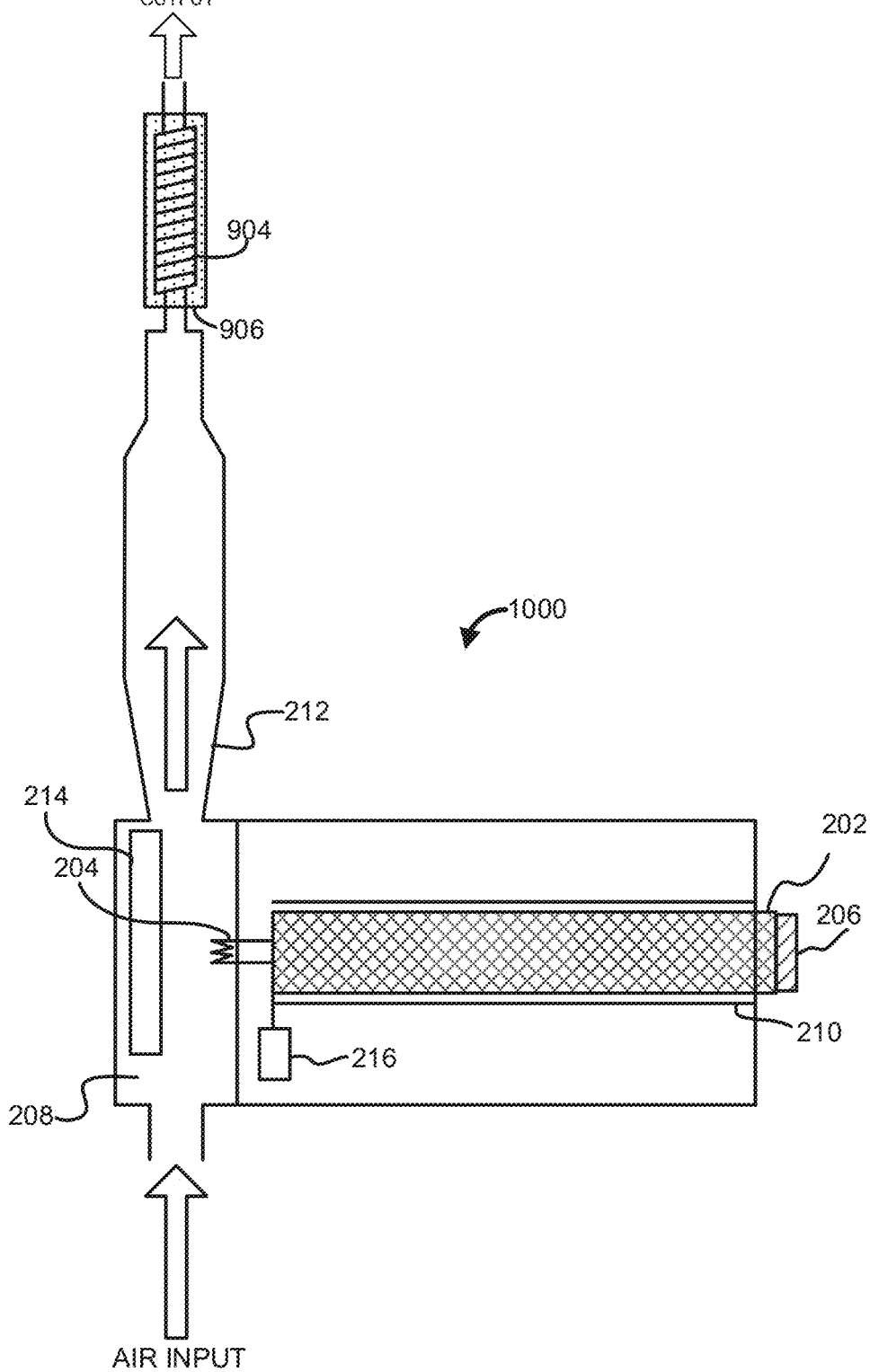
FIG. 10 illustrates another exemplary vaporizer configured for smooth vapor delivery.

FIG. 10 illustrates an exemplary vaporizer 1000. The vaporizer 1000 is another aspect of the exemplary vaporizer 900. The vaporizer 1000 illustrates that heated vapor exiting the exhaust port 212 can be received in to the coil 904. The temperature of the vapor is reduced as it travels through the coil 904. The coil 904 can be of any suitable length. In an aspect, the coil 904 can comprise any structure that accomplishes a cooling effect. For example, the coil 904 can be replaced with a screen with a mesh or grid-like structure, a conical structure, and/or a series of cooling airlocks, either stationary or opening, in a periscopic/telescopic manner. The coil 904 can be any shape and/or can take multiple forms capable of cooling heated vapor, which passes through its space.

In an aspect, the coil 904 can be cooled by a cooling element 906. In an aspect, the coil 904 and the cooling element 906 can be combined into a single cooling element. Accordingly, the temperature of vapor is reduced as it travels through the coil 904 prior to exiting an exhaust port 212. In an aspect, the cooling element 906 can be any suitable cooling system for use in a vapor device. For example, a fan, a heat sink, a liquid cooling system, a chemical cooling system, combinations thereof, and the like. In an aspect, the cooling element 906 can comprise a liquid cooling system whereby a fluid (e.g., water) passes through pipes in the vaporizer 1000. As this fluid passes around the coil 904, the fluid absorbs heat, cooling vapor in the coil 904. After the fluid absorbs the heat, the fluid can pass through a heat exchanger which transfers the heat from the fluid to air blowing through the heat exchanger. By way of further example, the cooling element 906 can comprise a chemical cooling system that utilizes an endothermic reaction. An example of an endothermic reaction, is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus the vaporizer 1000 can comprise a chamber for receiving the cooling element 906 in the form of a "cold pack." The cold pack can be activated prior to insertion into the vaporizer 1000 or can be activated after insertion through use of a button/switch and the like to mechanically activate the cold pack inside the vaporizer 1000.

In an aspect, the cooling element 906 and the coil 904 can be selectively moved within the vaporizer 1000 to control the temperature of the vapor. For example, the cooling element 906 and the coil 904 can be moved closer to the exhaust port 212 or further from the exhaust port 212 to regulate temperature. In another aspect, insulation can be incorporated as needed to maintain the integrity of heating and cooling, as well as absorbing any unwanted condensation due to internal or external conditions, or a combination thereof. The insulation can also be selectively moved within the vaporizer 1000 to control the temperature of the vapor. For example, the insulation can be moved to cover a portion, none, or all of the cooling element 906 and the coil 904 to regulate temperature.

Figure 11:
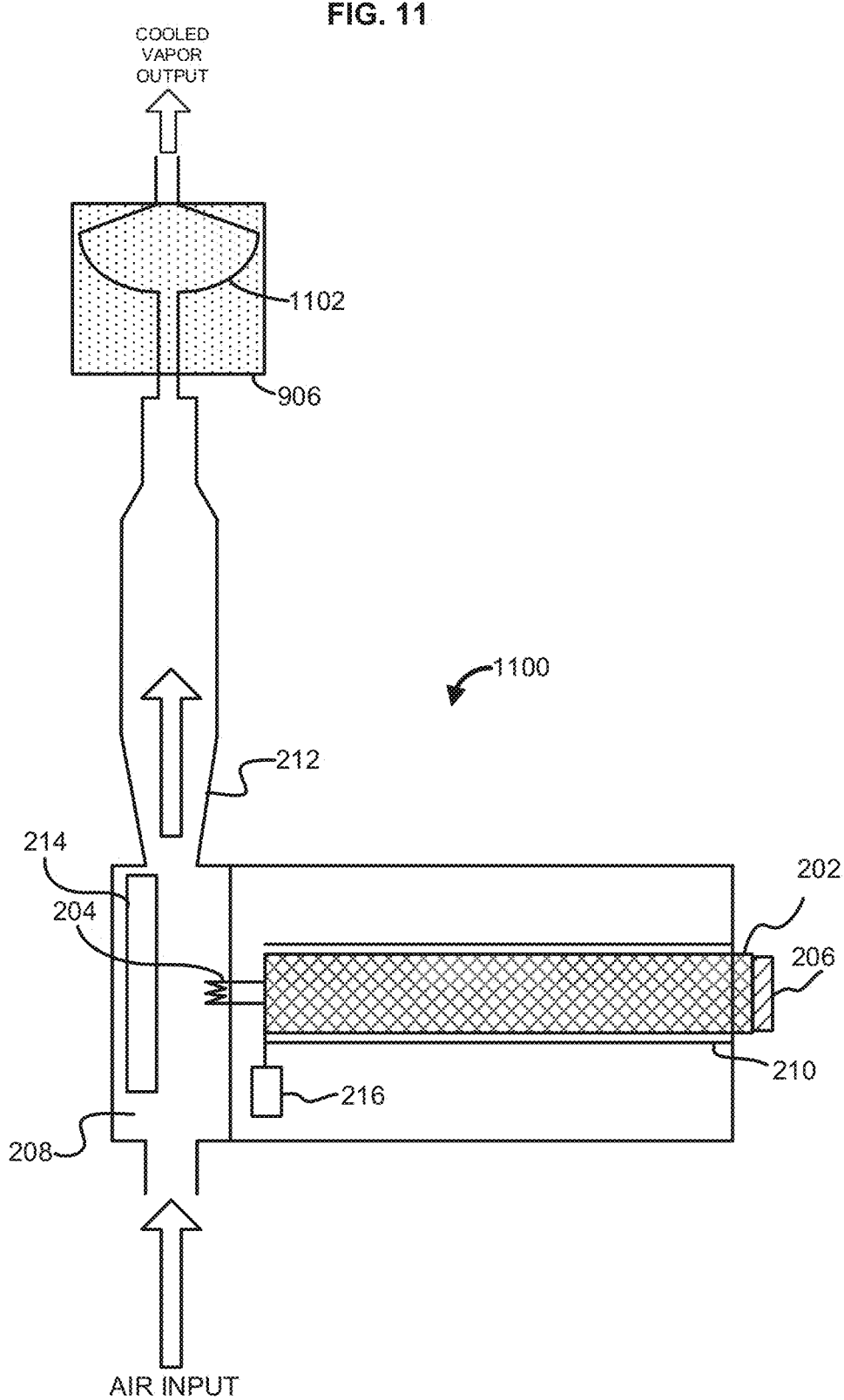
FIG. 11 illustrates another exemplary vaporizer configured for smooth vapor delivery.

FIG. 11 illustrates an exemplary vaporizer 1100. The vaporizer 1100 is another aspect of the exemplary vaporizer 200. The vaporizer 1100 illustrates that heated vapor exiting the exhaust port 212 can be received in to a cooling chamber/screen 1102. The temperature of the vapor is reduced as it travels through the cooling chamber/screen 1102. The cooling chamber/screen 1102 can be of any suitable size. In an aspect, the cooling chamber/screen 1102 can comprise any shape that accomplishes a cooling effect.

In an aspect, the cooling chamber/screen 1102 can be cooled by the cooling element 906. In an aspect, the cooling chamber/screen 1102 and the cooling element 906 can be combined into a single cooling element. Accordingly, the temperature of vapor is reduced as it travels through the cooling chamber/screen 1102 prior to exiting the exhaust port 212. In an aspect, the cooling element 906 can be any suitable cooling system for use in a vapor device. For example, a fan, a heat sink, a liquid cooling system, a chemical cooling system, combinations thereof, and the like. In an aspect, the cooling element 906 can comprise a liquid cooling system whereby a fluid (e.g., water) passes through pipes in the vaporizer 400. As this fluid passes around the cooling chamber/screen 1102, the fluid absorbs heat, cooling vapor in the cooling chamber/screen 1102. After the fluid absorbs the heat, the fluid can pass through a heat exchanger which transfers the heat from the fluid to air blowing through the heat exchanger. By way of further example, the cooling element 906 can comprise a chemical cooling system that utilizes an endothermic reaction. An example of an endothermic reaction is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus the vaporizer 1100 can comprise a chamber for receiving the cooling element 906 in the form of a "cold pack." The cold pack can be activated prior to insertion into the vaporizer 1100 or can be activated after insertion through use of a button/switch and the like to mechanically activate the cold pack inside the vaporizer 1100.

In an aspect, the cooling element 906 and the cooling chamber/screen 1102 can be selectively moved within the vaporizer 1100 to control the temperature of the vapor. For example, the cooling element 1106 and the cooling chamber/screen 1102 can be moved closer to the exhaust port 212 or further from the exhaust port 212 to regulate temperature. In another aspect, insulation can be incorporated as needed to maintain the integrity of heating and cooling, as well as absorbing any unwanted condensation due to internal or external conditions, or a combination thereof. The insulation can also be selectively moved within the vaporizer 1100 to control the temperature of the vapor. For example, the insulation can be moved to cover a portion, none, or all of the cooling element 906 and the cooling chamber/screen 1102 to regulate temperature.

Figure 12:
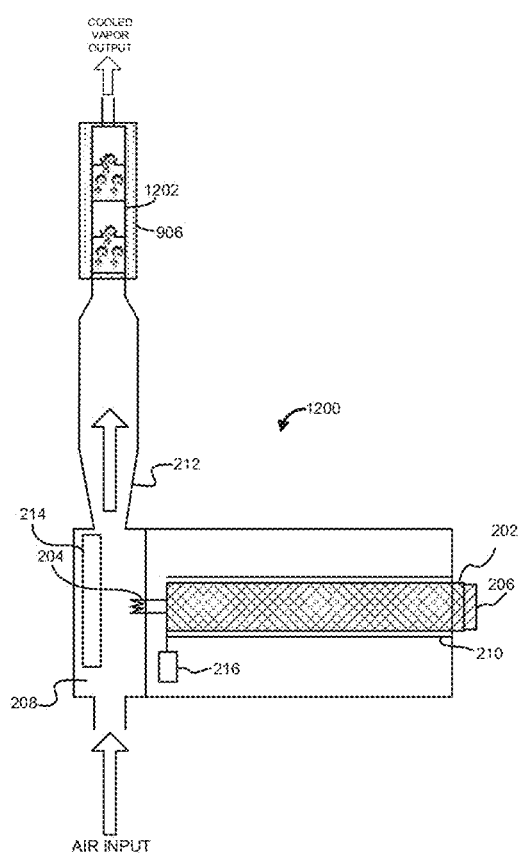
FIG. 12 illustrates another exemplary vaporizer configured for smooth vapor delivery.

FIG. 12 illustrates an exemplary vaporizer 1200. The vaporizer 1200 is another aspect of the exemplary vaporizer 200. The vaporizer 1200 illustrates that heated vapor exiting the exhaust port 212 can be received in to an airlock system 1202. The temperature of the vapor is reduced as it travels through one or more chambers of the airlock system 1202. The airlock system 1202 (including the one or more chambers) can be of any suitable size. In an aspect, the airlock system 1202 can comprise any shape that accomplishes a cooling effect. Heated vapor can pass into a chamber of the airlock system 1202 and remain in the chamber for a period of time. During that time the temperature of the vapor can be decreased. As a user inhales vapor, the airlock system 1202 can cause the vapor to move from one chamber to another causing a cooling effect as a result of delayed inhalation of the vapor.

In an aspect, the airlock system 1202 can be cooled by the cooling element 906. In an aspect, the airlock system 1202 and the cooling element 906 can be combined into a single cooling element. Accordingly, the temperature of vapor is reduced as it travels through the airlock system 1202 prior to exiting the exhaust port 212. In an aspect, the cooling element 906 can be any suitable cooling system for use in a vapor device. For example, a fan, a heat sink, a liquid cooling system, a chemical cooling system, combinations thereof, and the like. In an aspect, the cooling element 906 can comprise a liquid cooling system whereby a fluid (e.g., water) passes through pipes in the vaporizer 1200. As this fluid passes around the airlock system 1202, the fluid absorbs heat, cooling vapor in the airlock system 1202. After the fluid absorbs the heat, the fluid can pass through a heat exchanger which transfers the heat from the fluid to air blowing through the heat exchanger. By way of further example, the cooling element 906 can comprise a chemical cooling system that utilizes an endothermic reaction. An example of an endothermic reaction, is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus the vaporizer 1200 can comprise a chamber for receiving the cooling element 906 in the form of a "cold pack." The cold pack can be activated prior to insertion into the vaporizer 1200 or can be activated after insertion through use of a button/switch and the like to mechanically activate the cold pack inside the vaporizer 1200.

In another aspect, insulation can be incorporated as needed to maintain the integrity of heating and cooling, as well as absorbing any unwanted condensation due to internal or external conditions, or a combination thereof. The insulation can also be selectively moved within the vaporizer 300 to control the temperature of the vapor. For example, the insulation can be moved to cover a portion, none, or all of the cooling element 906 and the airlock system 1202 to regulate temperature.

Figure 13:
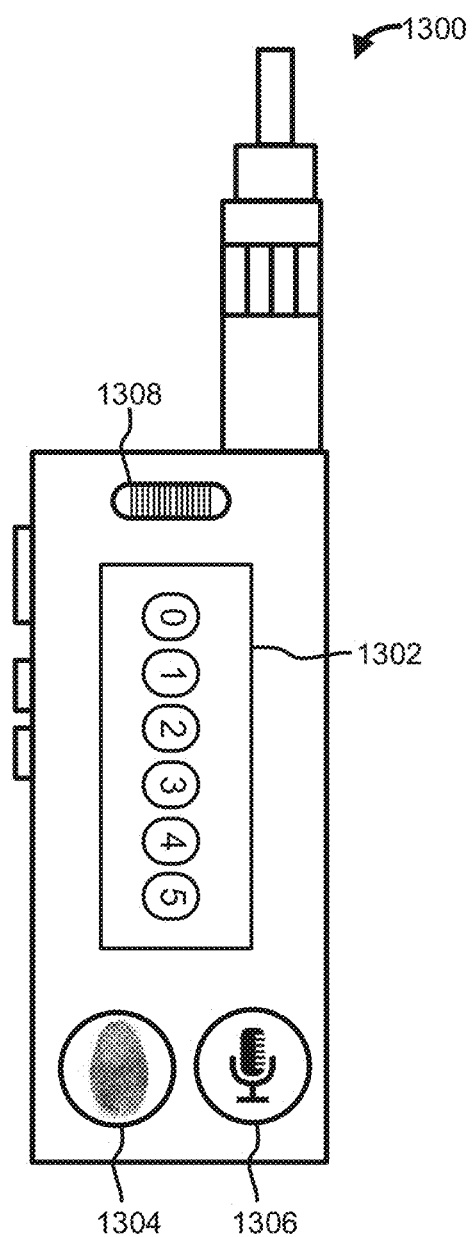
FIG. 13 illustrates an interface of an exemplary electronic vapor device.

FIG. 13 illustrates an exemplary vapor device 1300. The exemplary vapor device 1300 can comprise the vapor device 100 and/or any of the vaporizers disclosed herein. The exemplary vapor device 1300 illustrates a display 1302. The display 1302 can be a touchscreen. The display 1302 can be configured to enable a user to control any and/or all functionality of the exemplary vapor device 1300. For example, a user can utilize the display 1302 to enter a pass code to lock and/or unlock the exemplary vapor device 1300. The exemplary vapor device 1300 can comprise a biometric interface 1304. For example, the biometric interface 1304 can comprise a fingerprint scanner, an eye scanner, a facial scanner, and the like. The biometric interface 1304 can be configured to enable a user to control any and/or all functionality of the exemplary vapor device 1300. The exemplary vapor device 1300 can comprise an audio interface 1306. The audio interface 1306 can comprise a button that, when engaged, enables a microphone 1308. The microphone 1308 can receive audio signals and provide the audio signals to a processor for interpretation into one or more commands to control one or more functions of the exemplary vapor device 1300.

Figure 14:
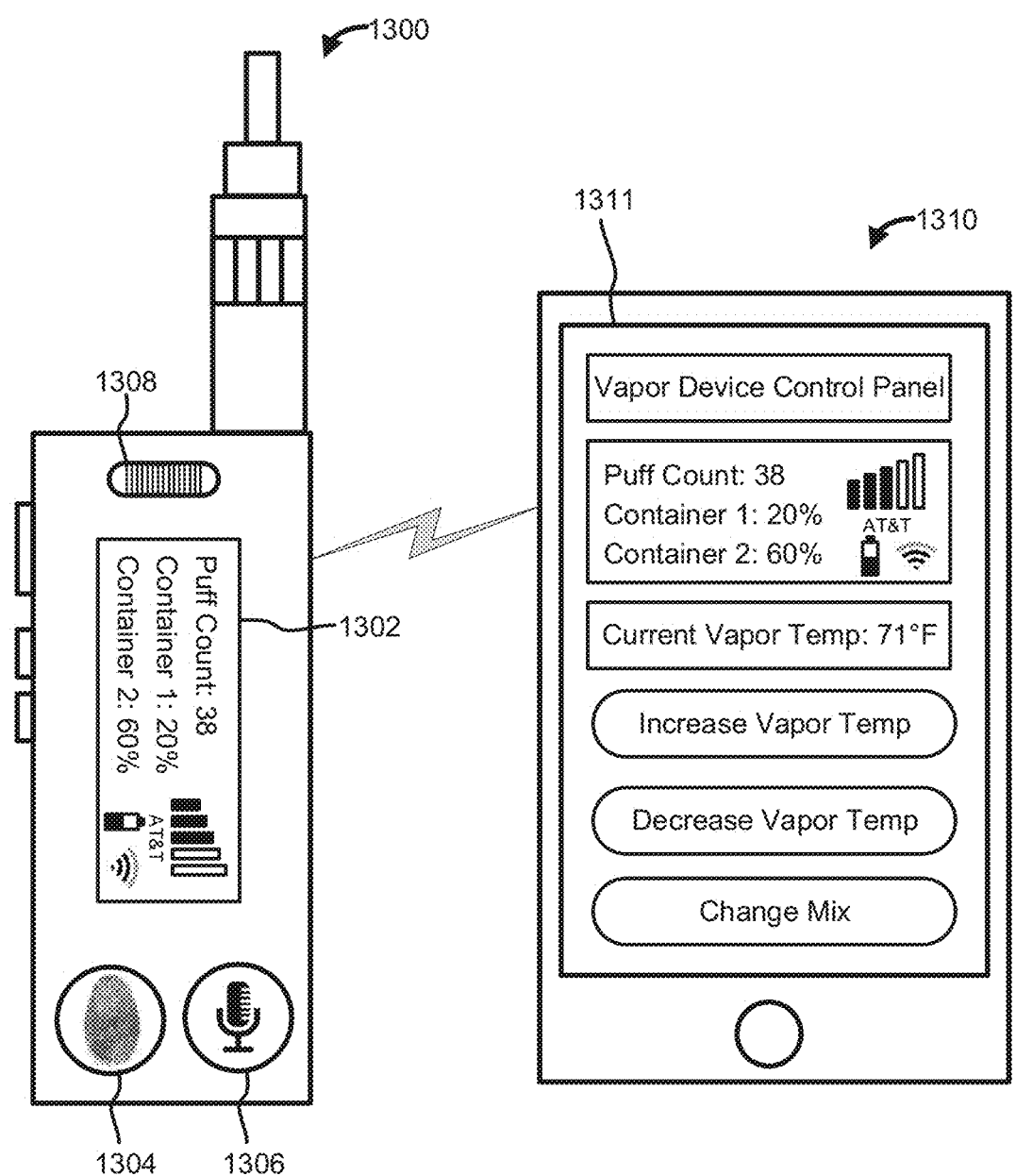
FIG. 14 illustrates another interface of an exemplary electronic vapor device.

FIG. 14 illustrates exemplary information that can be provided to a user via the display 1302 of the exemplary vapor device 1300 or via a display 1311 of an electronic device 1310 in communication with the exemplary vapor device 1300. The display 1302 can provide information to a user such as a puff count, an amount of vaporizable material remaining in one or more containers, battery remaining, signal strength, combinations thereof, and the like. The display 1311 can provide the same or different information to the user as available on the display 1302. In an aspect, the exemplary vapor device 1300 does not comprise the display 1302. The display 1311 can provide a user interface that provides information and provides control over one or more functions of the exemplary vapor device 1300. The one or more functions can comprise one or more of a community function, an e-commerce function, or a vapor device operability function. The community function can comprise at least one of a social networking function, transmitting or receiving a recommendation, transmitting or receiving a message, or transmitting or receiving a location of a user. The e-commerce function can comprise at least one of purchasing a component for use with the vapor device, purchasing a vaporizable or non-vaporizable material for use with the vapor device, purchasing another vapor device or components thereof, selling a component for use with the vapor device or another vapor device, selling a vaporizable or non-vaporizable material for use with the vapor device, or selling the vapor device or another vapor device. The device operability function can comprise at least one of controlling the vapor device, displaying diagnostic information, displaying repair information, displaying calibration information, displaying usage information, displaying a mixing interface to create/request a mixture, displaying an interface to adjust one or more vaporizing conditions (e.g., cooling element, temperature, and the like), or displaying information corresponding to detected constituents of material vaporized by the vapor device.

The user interface can comprise at least one of a lighted signal light, a gauge, a representation of a box, a representation of a form, a check mark, an avatar, a visual image, a graphic design, a list, an active calibration or calculation, a 2-dimensional fractal design, a 3-dimensional fractal design, a 2-dimensional representation of the vapor device or another vapor device, or a 3-dimensional representation of the vapor device or another vapor device. At least one of the 2-dimensional fractal design or the 3-dimensional fractal design can continuously or periodically expand or contract to various scales of the original fractal design.

Figure 15:
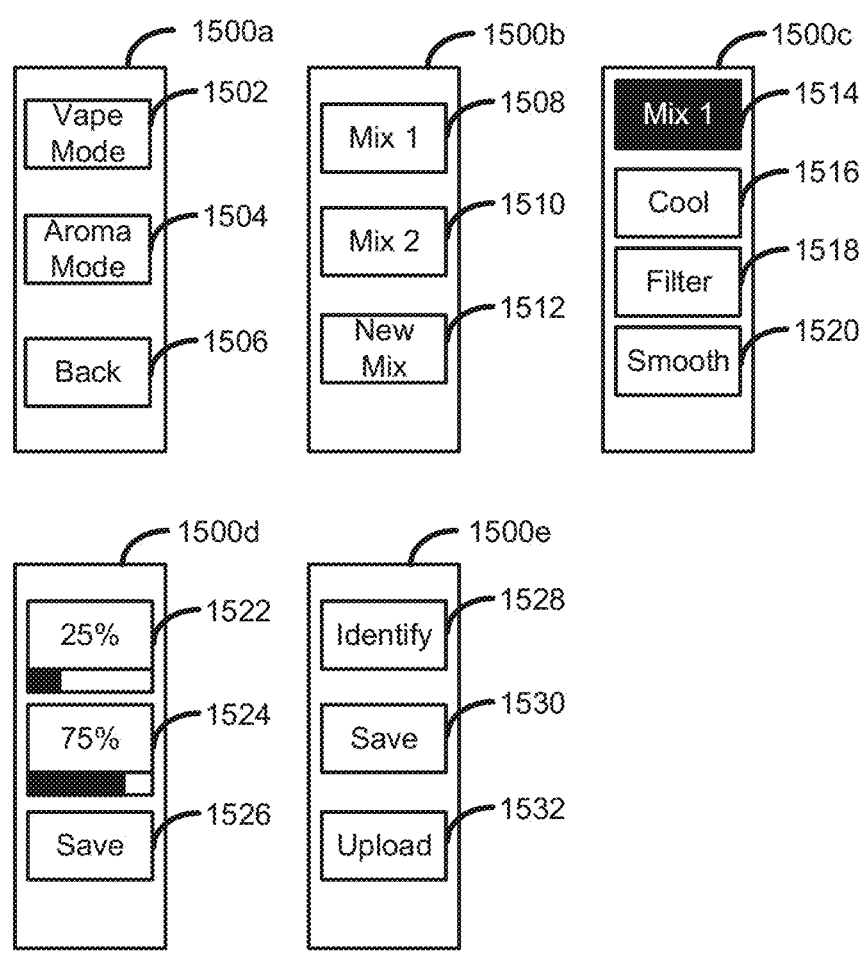
FIG. 15 illustrates several interfaces of an exemplary electronic vapor device.

FIG. 15 illustrates a series of user interfaces that can be provided via the display 1302 of the exemplary vapor device 1300 or via the display 1311 of the electronic device 1310 in communication with the exemplary vapor device 1300. In an aspect, the exemplary vapor device 1300 can be configured for one or more of multi-mode vapor usage. For example, the exemplary vapor device 1300 can be configured to enable a user to inhale vapor (vape mode) or to release vapor into the atmosphere (aroma mode). User interface 1500a provides a user with interface elements to select which mode the user wishes to engage, a Vape Mode 1502, an Aroma Mode 1504, or an option to go back 1506 and return to the previous screen. The interface element Vape Mode 1502 enables a user to engage a vaporizer to generate a vapor for inhalation. The interface element Aroma Mode 1504 enables a user to engage the vaporizer to generate a vapor for release into the atmosphere.

In the event a user selects the Vape Mode 1502, the exemplary vapor device 1300 will be configured to vaporize material and provide the resulting vapor to the user for inhalation. The user can be presented with user interface 1500b which provides the user an option to select interface elements that will determine which vaporizable material to vaporize. For example, an option of Mix 1 1508, Mix 2 1150, or a New Mix 1512. The interface element Mix 1 1508 enables a user to engage one or more containers that contain vaporizable material in a predefined amount and/or ratio. In an aspect, a selection of Mix 1 1508 can result in the exemplary vapor device 1300 engaging a single container containing a single type of vaporizable material or engaging a plurality of containers containing a different types of vaporizable material in varying amounts. The interface element Mix 2 1510 enables a user to engage one or more containers that contain vaporizable material in a predefined amount and/or ratio. In an aspect, a selection of Mix 2 1510 can result in the exemplary vapor device 1300 engaging a single container containing a single type of vaporizable material or engaging a plurality of containers containing a different types of vaporizable material in varying amounts. In an aspect, a selection of New Mix 1512 can result in the exemplary vapor device 1300 receiving a new mixture, formula, recipe, etc. . . . of vaporizable materials and/or engage one or more containers that contain vaporizable material in the new mixture.

Upon selecting, for example, the Mix 1 1508, the user can be presented with user interface 1500c. User interface 1500c indicates to the user that Mix 1 has been selected via an indicator 1514. The user can be presented with options that control how the user wishes to experience the selected vapor. The user can be presented with interface elements Cool 1516, Filter 1518, and Smooth 1520. The interface element Cool 1516 enables a user to engage one or more cooling elements to reduce the temperature of the vapor. The interface element Filter 1518 enables a user to engage one or more filter elements to filter the air used in the vaporization process. The interface element Smooth 1520 enables a user to engage one or more heating casings, cooling elements, filter elements, and/or magnetic elements to provide the user with a smoother vaping experience.

Upon selecting New Mix 1512, the user can be presented with user interface 1500d. User interface 1500d provides the user with a container one ratio interface element 1522, a container two ratio interface element 1524, and Save 1526. The container one ratio interface element 1522 and the container two ratio interface element 1524 provide a user the ability to select an amount of each type of vaporizable material contained in container one and/or container two to utilize as a new mix. The container one ratio interface element 1522 and the container two ratio interface element 1524 can provide a user with a slider that adjusts the percentages of each type of vaporizable material based on the user dragging the slider. In an aspect, a mix can comprise 100% on one type of vaporizable material or any percent combination (e.g., 50/50, 75/25, 85/15, 95/5, etc. . . . ). Once the user is satisfied with the new mix, the user can select Save 1526 to save the new mix for later use. In another aspect, any of the disclosed interface elements can comprise a slider, a dial, a numeric entry, combinations thereof, and the like. A mixture can comprise not only specific amounts of vaporizable materials to use in the mixture, but can further specify one or more vaporizing conditions. The one or more vaporizing conditions can comprise one or more of, application of a cooling element, application of a magnetic element, application of a smoothing element, a temperature the mixture should be vaporized at, and combinations thereof.

In the event a user selects the Aroma Mode 1504, the exemplary vapor device 1300 will be configured to vaporize material and release the resulting vapor into the atmosphere. The user can be presented with user interface 1500b, 1500c, and/or 1500d as described above, but the resulting vapor will be released to the atmosphere.

In an aspect, the user can be presented with user interface 1500e. The user interface 1500e can provide the user with interface elements Identify 1528, Save 1530, and Upload 1532. The interface element Identify 1528 enables a user to engage one or more sensors in the exemplary vapor device 1300 to analyze the surrounding environment. For example, activating the interface element Identify 1528 can engage a sensor to determine the presence of a negative environmental condition such as smoke, a bad smell, chemicals, etc. Activating the interface element Identify 1528 can engage a sensor to determine the presence of a positive environmental condition, for example, an aroma. The interface element Save 1530 enables a user to save data related to the analyzed negative and/or positive environmental condition in memory local to the exemplary vapor device 1300. The interface element Upload 1532 enables a user to engage a network access device to transmit data related to the analyzed negative and/or positive environmental condition to a remote server for storage and/or analysis.

Figure 16:
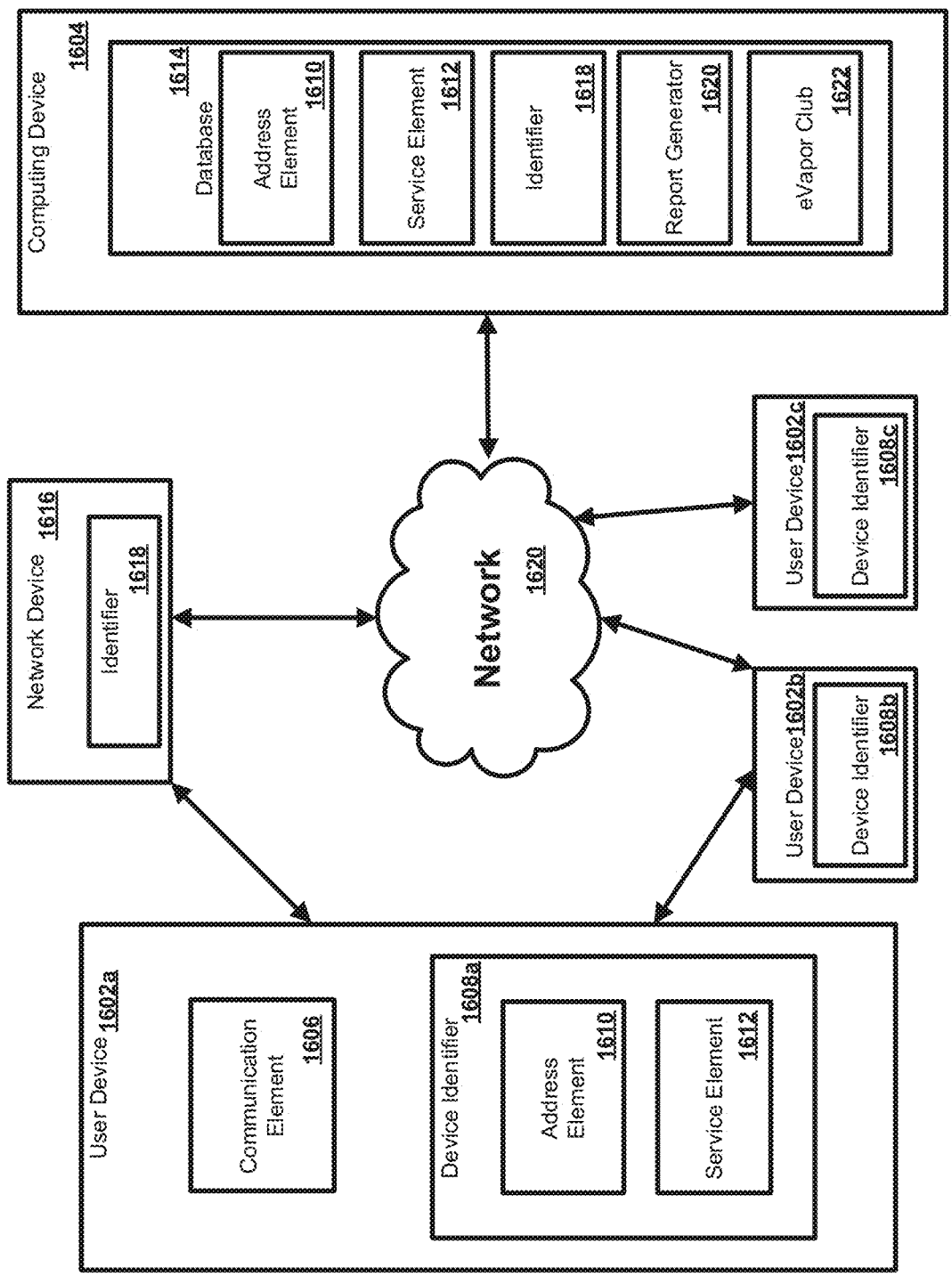
FIG. 16 illustrates an exemplary operating environment.

In one aspect of the disclosure, a system can be configured to provide services such as network-related services to a user device. FIG. 16 illustrates various aspects of an exemplary environment in which the present methods and systems can operate. The present disclosure is relevant to systems and methods for providing services to a user device, for example, electronic vapor devices which can include, but are not limited to, a vape-bot, micro-vapor device, vapor pipe, e-cigarette, hybrid handset and vapor device, and the like. Other user devices that can be used in the systems and methods include, but are not limited to, a smart watch (and any other form of "smart" wearable technology), a smartphone, a tablet, a laptop, a desktop, and the like. In an aspect, one or more network devices can be configured to provide various services to one or more devices, such as devices located at or near a premises. In another aspect, the network devices can be configured to recognize an authoritative device for the premises and/or a particular service or services available at the premises. As an example, an authoritative device can be configured to govern or enable connectivity to a network such as the Internet or other remote resources, provide address and/or configuration services like DHCP, and/or provide naming or service discovery services for a premises, or a combination thereof. Those skilled in the art will appreciate that present methods can be used in various types of networks and systems that employ both digital and analog equipment. One skilled in the art will appreciate that provided herein is a functional description and that the respective functions can be performed by software, hardware, or a combination of software and hardware.

The network and system can comprise a user device 1602a, 1602b, and/or 1602c in communication with a computing device 1604 such as a server, for example. The computing device 1604 can be disposed locally or remotely relative to the user device 1602a, 1602b, and/or 1602c. As an example, the user device 1602a, 1602b, and/or 1602c and the computing device 1604 can be in communication via a private and/or public network 1620 such as the Internet or a local area network. Other forms of communications can be used such as wired and wireless telecommunication channels, for example. In another aspect, the user device 1602a, 1602b, and/or 1602c can communicate directly without the use of the network 1620 (for example, via Bluetooth®, infrared, and the like).

In an aspect, the user device 1602a, 1602b, and/or 1602c can be an electronic device such as an electronic vapor device (e.g., vape-bot, micro-vapor device, vapor pipe, e-cigarette, hybrid handset and vapor device), a smartphone, a smart watch, a computer, a smartphone, a laptop, a tablet, a set top box, a display device, or other device capable of communicating with the computing device 1604. As an example, the user device 1602a, 1602b, and/or 1602c can comprise a communication element 1606 for providing an interface to a user to interact with the user device 1602a, 1602b, and/or 1602c and/or the computing device 1604. The communication element 1606 can be any interface for presenting and/or receiving information to/from the user, such as user feedback. An example interface can be communication interface such as a web browser (e.g., Internet Explorer, Mozilla Firefox, Google Chrome, Safari, or the like). Other software, hardware, and/or interfaces can be used to provide communication between the user and one or more of the user device 1602a, 1602b, and/or 1602c and the computing device 1604. In an aspect, the user device 1602a, 1602b, and/or 1602c can have at least one similar interface quality such as a symbol, a voice activation protocol, a graphical coherence, a startup sequence continuity element of sound, light, vibration or symbol. In an aspect, the interface can comprise at least one of lighted signal lights, gauges, boxes, forms, words, video, audio scrolling, user selection systems, vibrations, check marks, avatars, matrix', visual images, graphic designs, lists, active calibrations or calculations, 2D interactive fractal designs, 3D fractal designs, 2D and/or 3D representations of vapor devices and other interface system functions.

As an example, the communication element 1606 can request or query various files from a local source and/or a remote source. As a further example, the communication element 1606 can transmit data to a local or remote device such as the computing device 1604. In an aspect, data can be shared anonymously with the computing device 1604. The data can be shared over a transient data session with the computing device 1604. The transient data session can comprise a session limit. The session limit can be based on one or more of a number of puffs, a time limit, and a total quantity of vaporizable material. The data can comprise usage data and/or a usage profile. The computing device 1604 can destroy the data once the session limit is reached.

In an aspect, the user device 1602a, 1602b, and/or 1602c can be associated with a user identifier or device identifier 1608a, 1608b, and/or 1608c. As an example, the device identifier 1608a, 1608b, and/or 1608c can be any identifier, token, character, string, or the like, for differentiating one user or user device (e.g., user device 1602a, 1602b, and/or 1602c) from another user or user device. In a further aspect, the device identifier 1608a, 1608b, and/or 1608c can identify a user or user device as belonging to a particular class of users or user devices. As a further example, the device identifier 1608a, 1608b, and/or 1608c can comprise information relating to the user device such as a manufacturer, a model or type of device, a service provider associated with the user device 1602a, 1602b, and/or 1602c, a state of the user device 1602a, 1602b, and/or 1602c, a locator, and/or a label or classifier. Other information can be represented by the device identifier 1608a, 1608b, and/or 1608c.

In an aspect, the device identifier 1608a, 1608b, and/or 1608c can comprise an address element 1610 and a service element 1612. In an aspect, the address element 1610 can comprise or provide an internet protocol address, a network address, a media access control (MAC) address, an Internet address, or the like. As an example, the address element 1610 can be relied upon to establish a communication session between the user device 1602a, 1602b, and/or 1602c and the computing device 1604 or other devices and/or networks. As a further example, the address element 1610 can be used as an identifier or locator of the user device 1602a, 1602b, and/or 1602c. In an aspect, the address element 1610 can be persistent for a particular network.

In an aspect, the service element 1612 can comprise an identification of a service provider associated with the user device 1602a, 1602b, and/or 1602c and/or with the class of user device 1602a, 1602b, and/or 1602c. The class of the user device 1602a, 1602b, and/or 1602c can be related to a type of device, capability of device, type of service being provided, and/or a level of service. As an example, the service element 1612 can comprise information relating to or provided by a communication service provider (e.g., Internet service provider) that is providing or enabling data flow such as communication services to and/or between the user device 1602a, 1602b, and/or 1602c. As a further example, the service element 1612 can comprise information relating to a preferred service provider for one or more particular services relating to the user device 1602a, 1602b, and/or 1602c. In an aspect, the address element 1610 can be used to identify or retrieve data from the service element 1612, or vice versa. As a further example, one or more of the address element 1610 and the service element 1612 can be stored remotely from the user device 1602a, 1602b, and/or 1602c and retrieved by one or more devices such as the user device 1602a, 1602b, and/or 1602c and the computing device 1604. Other information can be represented by the service element 1612.

In an aspect, the computing device 1604 can be a server for communicating with the user device 1602a, 1602b, and/or 1602c. As an example, the computing device 1604 can communicate with the user device 1602a, 1602b, and/or 1602c for providing data and/or services. As an example, the computing device 1604 can provide services such as data sharing, data syncing, network (e.g., Internet) connectivity, network printing, media management (e.g., media server), content services, streaming services, broadband services, or other network-related services. In an aspect, the computing device 1604 can allow the user device 1602a, 1602b, and/or 1602c to interact with remote resources such as data, devices, and files. As an example, the computing device can be configured as (or disposed at) a central location, which can receive content (e.g., data) from multiple sources, for example, user devices 1602a, 1602b, and/or 1602c. The computing device 1604 can combine the content from the multiple sources and can distribute the content to user (e.g., subscriber) locations via a distribution system.

In an aspect, one or more network devices 1616 can be in communication with a network such as network 1620. As an example, one or more of the network devices 1616 can facilitate the connection of a device, such as user device 1602a, 1602b, and/or 1602c, to the network 1620. As a further example, one or more of the network devices 1616 can be configured as a wireless access point (WAP). In an aspect, one or more network devices 1616 can be configured to allow one or more wireless devices to connect to a wired and/or wireless network using Wi-Fi, Bluetooth or any desired method or standard.

In an aspect, the network devices 1616 can be configured as a local area network (LAN). As an example, one or more network devices 1616 can comprise a dual band wireless access point. As an example, the network devices 1616 can be configured with a first service set identifier (SSID) (e.g., associated with a user network or private network) to function as a local network for a particular user or users. As a further example, the network devices 1616 can be configured with a second service set identifier (SSID) (e.g., associated with a public/community network or a hidden network) to function as a secondary network or redundant network for connected communication devices.

In an aspect, one or more network devices 1616 can comprise an identifier 1618. As an example, one or more identifiers can be or relate to an Internet Protocol (IP) Address IPV4/IPV6 or a media access control address (MAC address) or the like. As a further example, one or more identifiers 1618 can be a unique identifier for facilitating communications on the physical network segment. In an aspect, each of the network devices 1616 can comprise a distinct identifier 1618. As an example, the identifiers 1618 can be associated with a physical location of the network devices 1616.

In an aspect, the computing device 1604 can manage the communication between the user device 1602a, 1602b, and/or 1602c and a database 1614 for sending and receiving data therebetween. As an example, the database 1614 can store a plurality of files (e.g., web pages), user identifiers or records, or other information. In one aspect, the database 1614 can store user device 1602a, 1602b, and/or 1602c usage information (including chronological usage), a status of a component of a device (e.g., coil failure), type of vaporizable and/or non-vaporizable material used, frequency of usage, location of usage, recommendations, communications (e.g., text messages, advertisements, photo messages), simultaneous use of multiple devices, one or more mixtures of vaporizable materials, and the like). The database 1614 can collect and store data to support cohesive use, wherein cohesive use is indicative of the use of a first electronic vapor devices and then a second electronic vapor device is synced chronologically and logically to provide the proper specific properties and amount of vapor based upon a designed usage cycle. As a further example, the user device 1602a, 1602b, and/or 1602c can request and/or retrieve a file from the database 1614. The user device 1602a, 1602b, and/or 1602c can thus sync locally stored data with more current data available from the database 1614. Such syncing can be set to occur automatically on a set time schedule, on demand, and/or in real-time. The computing device 1604 can be configured to control syncing functionality. For example, a user can select one or more of the user device 1602a, 1602b, and/or 1602c to never by synced, to be the master data source for syncing, and the like. Such functionality can be configured to be controlled by a master user and any other user authorized by the master user or agreement.

In an aspect, the computing device 1604 can grant access rights to one or more of the user device 1602a, 1602b, and/or 1602c to access certain information. For example, the computing device 1604 can receive a request from one or more of the user device 1602a, 1602b, and/or 1602c to have access to one or more mixtures of vaporizable materials stored at the computing device 1604. The computing device 1604 can be configured to process the request by debiting a financial account associated with the requesting user and providing an access token to the user's requesting device to unlock access to the requested mixture. A mixture stored on the computing device 1604 can be transmitted/shared at the request of one or more of the user device 1602a, 1602b, and/or 1602c that transmitted the mixture to the computing device 1604. The mixture can be sent to the one or more of the user device 1602a, 1602b, and/or 1602c at the request of the uploading device and/or at any user request. The mixture can be provided with a limited number of uses. The mixture can be transmitted so that the receiving user can vaporize according to the mixture to determine if the user enjoys the mixture. If the user desires to continue using the mixture, the user can request access rights. In some aspects, a commission can be paid to the user that submitted the mixture to the computing device 1604 for each other user that pays for the access rights to the mixture. A mixture can comprise not only specific amounts of vaporizable materials to use in the mixture, but can further specify one or more vaporizing conditions. The one or more vaporizing conditions can comprise one or more of, application of a cooling element, application of a magnetic element, application of a smoothing element, a temperature the mixture should be vaporized at, and combinations thereof.

By way of example, usage information may include demographic information or other information about a user of the user device 1602a, 1602b, and/or 1602c. Demographic information can comprise one or more of a user's: age, gender, race, education level, location of residence, income, employment status, religion, marital status, property ownership, or known languages. The demographic information can be reported to the computing device 1604 if the user has opted in to having their usage activity tracked. For example, this information may be provided from the user device 1602a, 1602b, and/or 1602c to the computing device 1604 at opt-in time. The computing device 1604 may store the demographic information in the database 1614. In various embodiments, the demographic information may be associated with an identifier of the user for easy retrieval. For instance, all records for a specific user may be associated with a user's identifier. As the computing device 1604 stores the demographic information for later use, the demographic information need not be provided during vapor usage that occurs subsequent to the user's initial opt-in. Although it should be understood that the user of the user device 1602a, 1602b, and/or 1602c may provide updated demographic information at their discretion and/or at the request of the computing device 1604. In various embodiments, the demographic information may include but is not limited to information about a user's age, gender, education level, location of residence, income, employment status, religion, marital status, ownership (e.g., home, car, etc.), and known languages. This information may be utilized to generate reports for specific groups. In one non-limiting example, demographic information may be utilized to identify a group of users as young adults living in urban areas. For instance, a report generated for this group of users might specify the most popular vaporizable materials consumed by young adults living in urban areas. In an aspect, users may be tracked by a global identifier instead of personally identifiable information (e.g., the user's name). Thus the identifier can be known to the computing device 1604 but anonymous or otherwise unknown to other entities.

In an aspect, the computing device 1604 can generate recommendation data. The recommendation data can comprise a recommendation for a vaporizable material that a user has not used, a recommendation for a vaporizable material that a user has used, a recommendation for a mixture of two or more vaporizable materials that a user has not used, a recommendation for a mixture of two or more vaporizable materials that a user has used, a recommendation for a brand, a recommendation for a sale, a recommendation for a retailer, a recommendation for a manufacturer, a recommendation for an event, a recommendation for a social network, or a combination thereof. The central server can determine the recommendation data based on data received from at least one of a retailer, a manufacturer, an electronic device user, a vapor device user, a social network, or a combination thereof. The recommendation data can be generated in response to receiving usage data from the user device 1602a, 1602b, and/or 1602c and can be provided back to one or more of the user device 1602a, 1602b, and/or 1602c.

The computing device 1604 can utilize one or more recommendation systems/methods. For example, the computing device 1604 can utilize a non-personalized systems recommend products to individual consumers based on averaged information about the products provided by other consumers. Examples of non-personalized product recommendation systems are those of Amazon.com and Moviefinder.com. The same product recommendations are made to all consumers seeking information about a particular product(s) and all product recommendations are completely independent of any particular consumer.

The computing device 1604 can utilize an item-to-item systems recommend other products to an individual consumer based on relationships between products already purchased by the consumer or for which the consumer has expressed an interest. The relationships employed typically are brand identity, fragrance, sales appeal, market distribution, and the like. In all cases the information on which the relationships are based is implicit. In other words, no explicit input regarding what the consumer is looking for or prefers is solicited by these systems. Rather, techniques such as data mining are employed to find implicit relationships between products for which the individual consumer has expressed a preference and other products available for purchase. The actual performance of products or whether the consumer (or other consumers) ultimately did prefer the products purchased play no part in formulating recommendations with these types of systems.

The computing device 1604 can utilize an attribute-based recommendation systems utilize syntactic properties or descriptive "content" of available products to formulate their recommendations. In other words, attribute-based systems assume that the attributes of products are easily classified and that an individual consumer knows which classification he or she should purchase without help or input from the recommendation system.

The computing device 1604 can utilize a content-based filtering recommendation systems are based on a description of the item and a profile of the user's preference. In a content-based recommender system, keywords are used to describe the items and a user profile is built recommendation system indicate the type of item this user likes. In other words, these algorithms try to recommend items that are similar to those that a user liked in the past (or is examining in the present). In particular, various candidate items are compared with items previously rated by the user and the best-matching items are recommended.

The computing device 1604 can utilize a collaborative filtering (also referred to as social-information filtering) recommendation system that typically records an extended product preference set that can be matched with a collaborative group. In other words, collaborative filters recommend products that "similar users" have rated highly. Often the social-information is a similar pattern of product preferences.

In an aspect, data can be derived by system and/or device analysis. Such analysis can comprise at least by one of instant analysis performed by the user device 1602a, 1602b, and/or 1602c or archival data transmitted to a third party for analysis and returned to the user device 1602a, 1602b, and/or 1602c and/or computing device 1604. The result of either data analysis can be communicated to a user of the user device 1602*a*, 1602*b*, and/or 1602*c* to, for example, inform the user of their eVapor use and/or lifestyle options. In an aspect, a result can be transmitted back to at least one authorized user interface.

In an aspect, the database 1614 can store information relating to the user device 1602*a*, 1602*b*, and/or 1602*c* such as the address element 1610 and/or the service element 1612. As an example, the computing device 1604 can obtain the device identifier 1608*a*, 1608*b*, and/or 1608*c* from the user device 1602*a*, 1602*b*, and/or 1602*c* and retrieve information from the database 1614 such as the address element 1610 and/or the service elements 1612. As a further example, the computing device 1604 can obtain the address element 1610 from the user device 1602*a*, 1602*b*, and/or 1602*c* and can retrieve the service element 1612 from the database 1614, or vice versa. Any information can be stored in and retrieved from the database 1614. The database 1614 can be disposed remotely from the computing device 1604 and accessed via direct or indirect connection. The database 1614 can be integrated with the computing device 1604 or some other device or system. Data stored in the database 1614 can be stored anonymously and can be destroyed based on a transient data session reaching a session limit.

All the various data/information may be utilized by a report generator 1620 to generate reports for specific groups of users. In one example, the collected usage information, demographic information, and recommendation information can be associated with a user's identifier. The report generator 1620 can be configured for determining characteristics of a group. In various embodiments, these characteristics may be specified by a user desiring the report. In other cases, the characteristics may be parameters stored locally (e.g., on the computing device 1604 or another system). In various embodiments, such characteristics may include a specific demographic population. For instance, a non-limiting example of such characteristics might include all males between the ages of 18 and 32 living in the United States. Of course this is just one example of such characteristics. In general, any subset of demographic information may be specified as characteristics of a group. For instance, different advertisers may be interested in different types of groups for their products.

The report generator 1620 can be configured for defining a group as a subset of users having one or more of the characteristics. For instance, a user can search the database 1614 for all users that match the characteristics based on the demographic data collected (e.g., demographic data collected when the user opts-in to having their usage activities monitored/tracked). For instance, for the example above that specifies characteristics as being all males between the ages of 18 and 32 living in the United States, the report generator 1620 can search demographic information for users meeting these characteristics; the results list of users may be defined as the group for which a report is to be generated.

The report generator 1620 can be configured for generating a usage report based on collected usage information for users of the defined group. In various embodiments, the report may specify aggregate attributes for the group, such as what vaporizable material, what vapor device, what types of vaporizable material the group vaporizes most frequently, and the like. For instance, the report may specify a ranking of the most popular vaporizable materials consumed by users of the defined group. In other examples, the report may be more general in that types of vaporizable material (e.g., fruit flavored, menthol, nicotine, etc.) are ranked instead of specific vaporizable materials. As one non-limiting example, such a report might demonstrate that males between the ages of 18 and 32 living in the United States favor vaporizable material with nicotine over vaporizable material without. In general, the report may specify absolute and/or relative rankings for vaporizable material and/or types of vaporizable material, and any other rankable/measurable data point available in the usage data.

In various embodiments, the generated reports may be used by advertisers to select which vaporizable materials should be pursued for advertising. For instance, if an advertiser is targeting a demographic including males between the ages of 18 and 32 living in the United States, the advertiser could use the example report described above to target advertisements for specific products of interest to the group (including delivering an advertisement directly to the group's electronic vapor devices).

In an aspect, the computing device 1604 can comprise one or more modules for managing an eVapor Club 1620. The eVapor Club 1620 can be configured for conducting one or more financial transactions. For example, the eVapor Club 1620 can be configured to periodically debit one or more users' financial accounts for membership in the eVapor Club 1620 (including debiting at different amounts to account for different tiers of membership within the eVapor Club 1620). The eVapor Club 1620 can also be configured to debit one or more users' financial accounts for goods on as needed basis. The eVapor Club 1620 can be configured for analyzing one or more of usage data, demographic data, and user preferences to determine a good(s) to transfer to a user. Examples of user preferences include, but are not limited to, one or more of a tier of membership in an electronic vapor (eVapor) club, a time interval for periodic delivery of the good, a preferred retail location, a preferred delivery location. In one aspect, the eVapor Club 1620 can periodically initiate a transfer of a good to a user according to the user's tier of membership in the eVapor Club 1620 (e.g., cause a low, middle, or high quality vaporizable material to be mailed to the user or setup for pickup by the user at a retail location). The eVapor Club 1620 can select the good according to usage data (e.g., is the user low on a particular vaporizable material) and recommendation data (e.g., what other flavor of vaporizable material might the user like) and user preferences (e.g., has the user indicated a preference for one or more types of vaporizable materials). In another aspect, the eVapor Club 1620 can analyze usage data to determine if the user's is in particular need for a specific good (e.g., a replacement component for the electronic vapor device).

Figure 17:
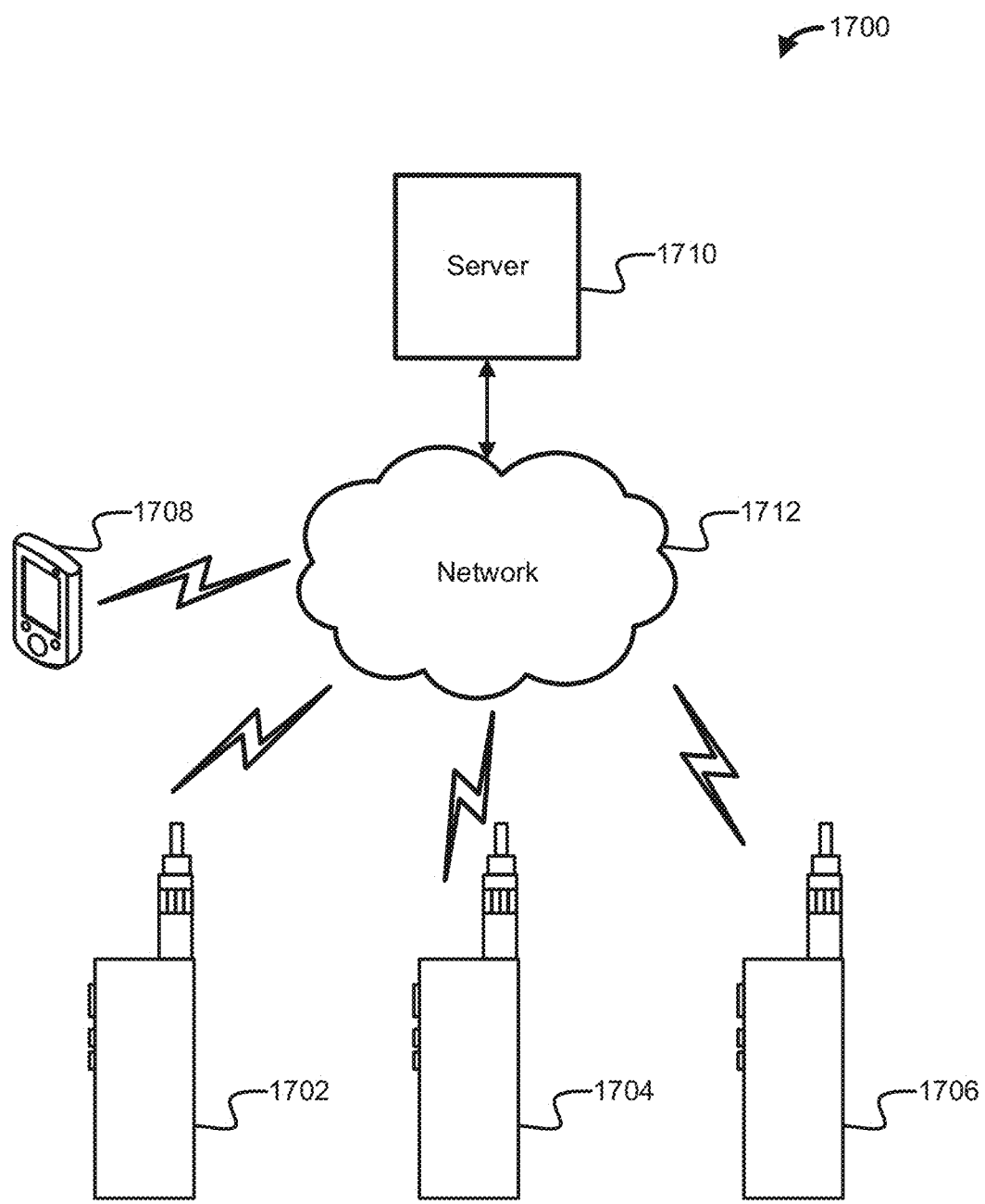
FIG. 17 illustrates another exemplary operating environment.
Figure 18:
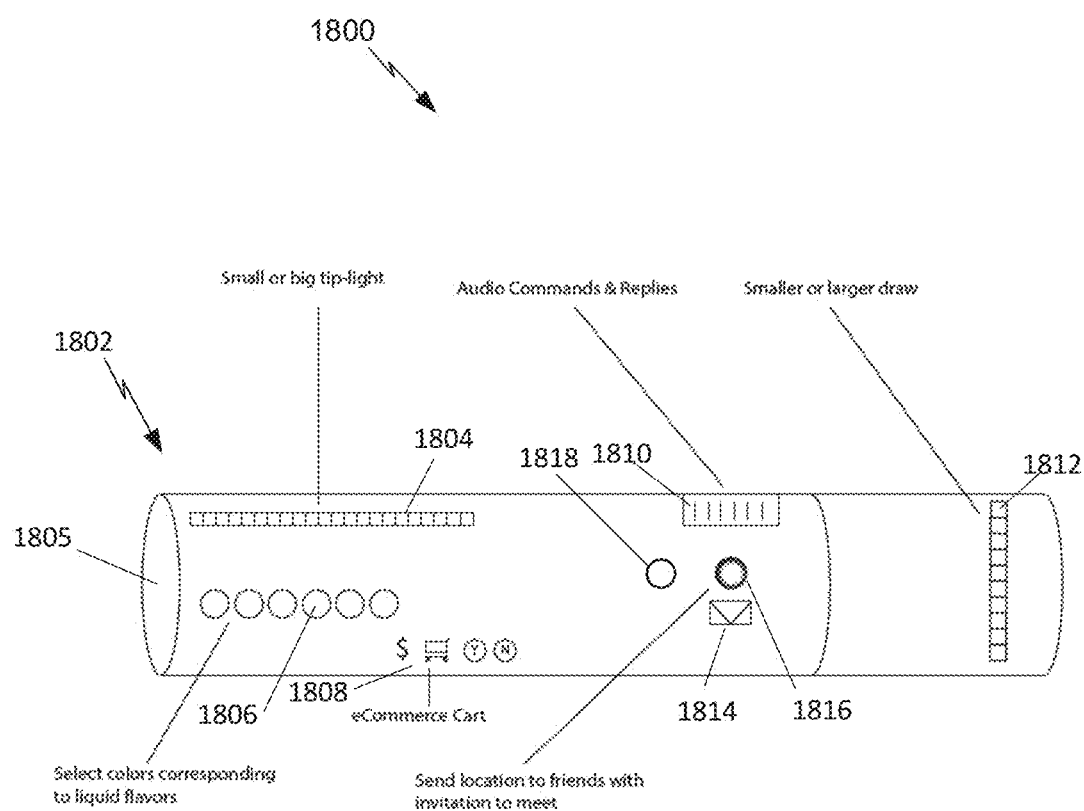
FIG. 18 illustrates an exemplary electronic vaporizer device.

FIG. 17 illustrates an ecosystem 1700 configured for sharing and/or syncing data, and/or generating reports based on the data, such as usage information (including chronological usage), a status of a component of a device (e.g., coil failure), type of vaporizable and/or non-vaporizable material used, frequency of usage, location of usage, recommendation data, communications (e.g., text messages, advertisements, photo messages), simultaneous use of multiple devices, and the like) between one or more devices such as a vapor device 1702, a vapor device 1704, a vapor device 1706, and an electronic communication device 1708. In an aspect, the vapor device 1702, the vapor device 1704, the vapor device 1706 can be one or more of an e-cigarette, an e-cigar, an electronic vapor modified device, a hybrid electronic communication handset coupled/integrated vapor device, a micro-sized electronic vapor device, or a robotic vapor device. In an aspect, the electronic communication device 1708 can comprise one or more of a smartphone, a smart watch, a tablet, a laptop, and the like.

In an aspect data generated, gathered, created, etc., by one or more of the vapor device 1702, the vapor device 1704, the vapor device 1706, and/or the electronic communication device 1708 can be uploaded to and/or downloaded from a central server 1710 via a network 1712, such as the Internet. Such uploading and/or downloading can be performed via any form of communication including wired and/or wireless. In an aspect, the vapor device 1702, the vapor device 1704, the vapor device 1706, and/or the electronic communication device 1708 can be configured to communicate via cellular communication, WiFi communication, Bluetooth® communication, satellite communication, and the like. The central server 1710 can store uploaded data and associate the uploaded data with a user and/or device that uploaded the data. The central server 1710 can access unified account and tracking information to determine devices that are associated with each other, for example devices that are owned/used by the same user. The central server 1710 can utilize the unified account and tracking information to determine which of the vapor device 1702, the vapor device 1704, the vapor device 1706, and/or the electronic communication device 1708, if any, should receive data uploaded to the central server 1710. In an aspect, the central server 1710 can be configured to operate as an eVapor Club as described herein.

In an aspect, the uploading and downloading can be performed anonymously. The data can be shared over a transient data session with the central server 1710. The transient data session can comprise a session limit. The session limit can be based on one or more of a number of puffs, a time limit, and a total quantity of vaporizable material. The data can comprise usage data and/or a usage profile. The central server 1710 can destroy the data once the session limit is reached. While the transient data session is active, the central server 1710 can provide a usage profile to one of the vapor device 1702, the vapor device 1704, the vapor device 1706 to control the functionality for the duration of the transient data session.

For example, the vapor device 1702 can be configured to upload usage information related to vaporizable material consumed and the electronic communication device 1708 can be configured to upload location information related to location of the vapor device 1702. The central server 1710 can receive both the usage information and the location information, access the unified account and tracking information to determine that both the vapor device 1702 and the electronic communication device 1708 are associated with the same user. The central server 1710 can thus correlate the user's location along with the type, amount, and/or timing of usage of the vaporizable material. The central server 1710 can further determine which of the other devices are permitted to receive such information and transmit the information based on the determined permissions. In an aspect, the central server 1710 can transmit the correlated information to the electronic communication device 1708 which can then subsequently use the correlated information to recommend a specific type of vaporizable material to the user when the user is located in the same geographic position indicated by the location information.

In an aspect, one or more of the vapor device 1702, the vapor device 1704, and/or the vapor device 1706 can provide the respective users with an option to have usage activity tracked (e.g., upload usage data to the central server 1710). For example, if a user opts in to having usage activity tracked, the user can also provide demographic information about the user to the central server 1710. Demographic information can comprise one or more of a user's: age, gender, race, education level, location of residence, income, employment status, religion, marital status, property ownership, or known languages. The collected demographic information and the usage data can be utilized to generate one or more usage reports representing usage across one or more of the users of the vapor device 1702, the vapor device 1704, and/or the vapor device 1706.

In another aspect, the central server 1710 can provide one or more social networking services for users of the vapor device 1702, the vapor device 1704, the vapor device 1706, and/or the electronic communication device 1708. Such social networking services include, but are not limited to, messaging (e.g., text, image, and/or video), mixture sharing, product recommendations, location sharing, product ordering, and the like.

In an aspect, the vapor device 1702, the vapor device 1704, and/or the vapor device 1706 can be in communication with the electronic communication device 1708 to enable the electronic communication device 1708 to generate a user interface to display information about and to control one or more functions/features of the vapor device 1702, the vapor device 1704, and/or the vapor device 1706. The electronic communication device 1708 can request access to one or more of the vapor device 1702, the vapor device 1704, and/or the vapor device 1706 from the central server 1710. The central server 1710 can determine whether or not the electronic communication device 1708 (or a user thereof) is authorized to access the one or more of the vapor device 1702, the vapor device 1704, and/or the vapor device 1706. If the central server 1710 determines that access should be granted, the central server 1710 can provide an authorization token to the electronic communication device 1708 (or to the vapor device 1702, the vapor device 1704, and/or the vapor device 1706 on behalf of the electronic communication device 1708). Upon receipt of the authorization token, the one or more of the vapor device 1702, the vapor device 1704, and/or the vapor device 1706 can partake in a communication session with the electronic communication device 1708 whereby the electronic communication device 1708 generates a user interface that controls one or more functions/features of and displays information about the one or more of the vapor device 1702, the vapor device 1704, and/or the vapor device 1706.

Referring to FIG. 14, aspects of a system 1800 for implementing an intuitive user interface are illustrated. A system 1800 may include, for example, an eVapor device 1802. In some versions the eVapor device 1802 comprises one of: a personal vaporizer, a smokeless pipe, an e-cigarette, an e-cigar, an eVapor pipe, a micro-eVapor device, a hybrid electronic communication and eVapor device, a vape Bot, a headset, and a monocle. Moreover, the eVapor apparatus 1802 can comprise any suitable component for providing vapor to a user. Generally, an eVapor device is an electronic device for use in providing a vapor output and typically includes a processor.

The eVapor device 1802 can comprise a plurality of intuitive buttons 1804-1818. The intuitive buttons can be symbols, icons, touch-sensitive, tactile, LED lights, etc., or any type of interactive button known in the art.

Tip control lights 1804 can be used to determine a brightness level of the tip light 1805 of the eVapor device 1802. For example, as commonly known in the art, an eVapor device 1802 comprises a tip light 1805 located at the tip of the eVapor device 1802, opposite of where a user inhales. The brightness and color of the tip light 1805 can be controlled using tip control lights 1804. For example, tip control lights 1804 can comprise a plurality of LED lights arranged linearly in a row, and the user can slide his/her finger across the lights in order to control the brightness and color of the tip light 1805. In some versions, tip control lights 1804 and tip light 1805 can be a variety of colors from the full spectrum of the rainbow.

Liquid flavor lights 1806 can be used to determine which flavors of eLiquid are being used. For example, liquid flavor lights 1806 can comprise a plurality of LED lights arranged linearly in a row. The liquid flavor lights 1806 can each be different colors, with each color corresponding to a different eLiquid flavor. By toggling different combinations of the liquid flavor lights 1806, the user can choose a variety of mixes of eLiquids to vaporize.

Icons 1808 can be used for E-commerce purposes. For example, icons 1808 can comprise shapes, symbols, and buttons, including, but not limited to, a dollar sign symbol, a shopping cart icon, and "Yes" and "No" buttons. Icons 1808 can be toggled in order to complete purchases online from an E-commerce vendor. Toggling icons 1808 will display information regarding the particular icon toggled. For example, the dollar sign will show how much something costs, the shopping cart will display the user's shopping cart, and the "Yes" and "No" buttons can be used to complete or cancel a transaction.

Audio command input 1810 can be used to give verbal commands to eVapor device 1802. For example, audio command input 1810 can comprise a microphone and speaker as commonly known in the art. For commands a user wants to issue to eVapor device, the user can talk into audio command input 1810, similar to methods well-known in the art for smartphones.

Draw lights 1812 can be used to determine how large of a drag the user takes from the eVapor device 1802. For example, draw lights 1812 can comprise a plurality of LED lights arranged linearly in a row. As the user takes a drag, each individual light can light up one at a time, one after another. The larger the drag, the more lights light up. This can indicate to the user how large of a drag, and how deep the inhalation per drag. Alternatively, a drag limit can be selected using draw lights 1812 in order to limit how large or small of a drag the user takes. In some versions, the draw lights 1812 can comprise different colors of lights, for example, ranging from a spectrum of dark to light colors.

Correspondence button 1818 can be used to indicate receipt of correspondence from other users. For example, correspondence button 1818 can be an envelope icon, indicating receipt of E-mail. Other icons can be used to indicate different messages. For example, emoji's, such as a happy face or sad face, can be displayed, as well as simple animations.

Location button 1816 can be used to send the user's location to friends in order to generate an invitation to meet. Location button 1816 can be an icon shaped like a house, or any other object correlating to a location.

Cooling button 1818 can be used to activate/de-activate a vapor cooling function. The cooling button 1818 can further be used to control an amount of vapor cooling applied (e.g., by holding down the cooling button 1818).

In use, eVapor device 1802 can be used to unlock and mix customized eLiquid combinations via an E-commerce service. For example, certain eLiquids can be unlocked by purchasing them from an E-commerce site using the intuitive interface 1802. Once unlocked, the eLiquid can be used by the user. In some versions, the eLiquid is locally available at the eVapor device 1802, such that the user does not have to await delivery in the mail. In some versions, the user can mix his/her own eLiquid mix using liquid flavor lights 1806. For example, the exact specifications of the user's custom flavor mix are transmitted to an E-commerce fulfillment center, so that the eLiquid provider can mix the custom eLiquid mix in a cartridge for the user. The custom mix is thereafter available to the user for re-ordering, or to be sent as a gift to friends. Alternatively, the mixing recipe can also be sent to friends, such that the friends can sample the custom mix to make alterations of their own for saving. As such, a user can create a custom mix from scratch, or can have the custom mix defined by parts, such as one part flavor A and two parts flavor B, etc. The interface 1800 also allows a user to customize messages to a plurality of other users, to join eVapor clubs, to receive eVapor chart information, and to conduct a wide range of social networking functions, location services, and eCommerce activities.

In related aspects, the liquid mix can be adapted to vaporize into a mixed aroma for the purpose of aromatherapy. For example, the aromatherapy can comprise imparting a prescribed aroma into a specified space utilizing the electronic vaporizing device as a distribution medium for the prescribed aroma. The electronic vaporizing device can be at least one of an eCig, a robotic electronic vaporizing device, a hybrid communication handset vaporizing device, or other electronic vaporing devices.

Various electronic personal vaporizing devices are known in the art, and are frequently being improved on. For example, details of a recent "Vapor Delivery Device" are disclosed by the inventor hereof in U.S. Patent Publication No. 2015/0047661, incorporated herein by reference. While the referenced publication provides a pertinent example of a personal vaporizer, it should be appreciated that various different designs for personal vaporizing devices are known in the art and may be adapted for use with the technology disclosed herein by one of ordinary skill. In addition, similar portable and personal devices for nebulizing liquids to create a mist for inhalation should be considered as generally encompassed within the meaning of "personal vaporizer" as used herein.

Figure 19:
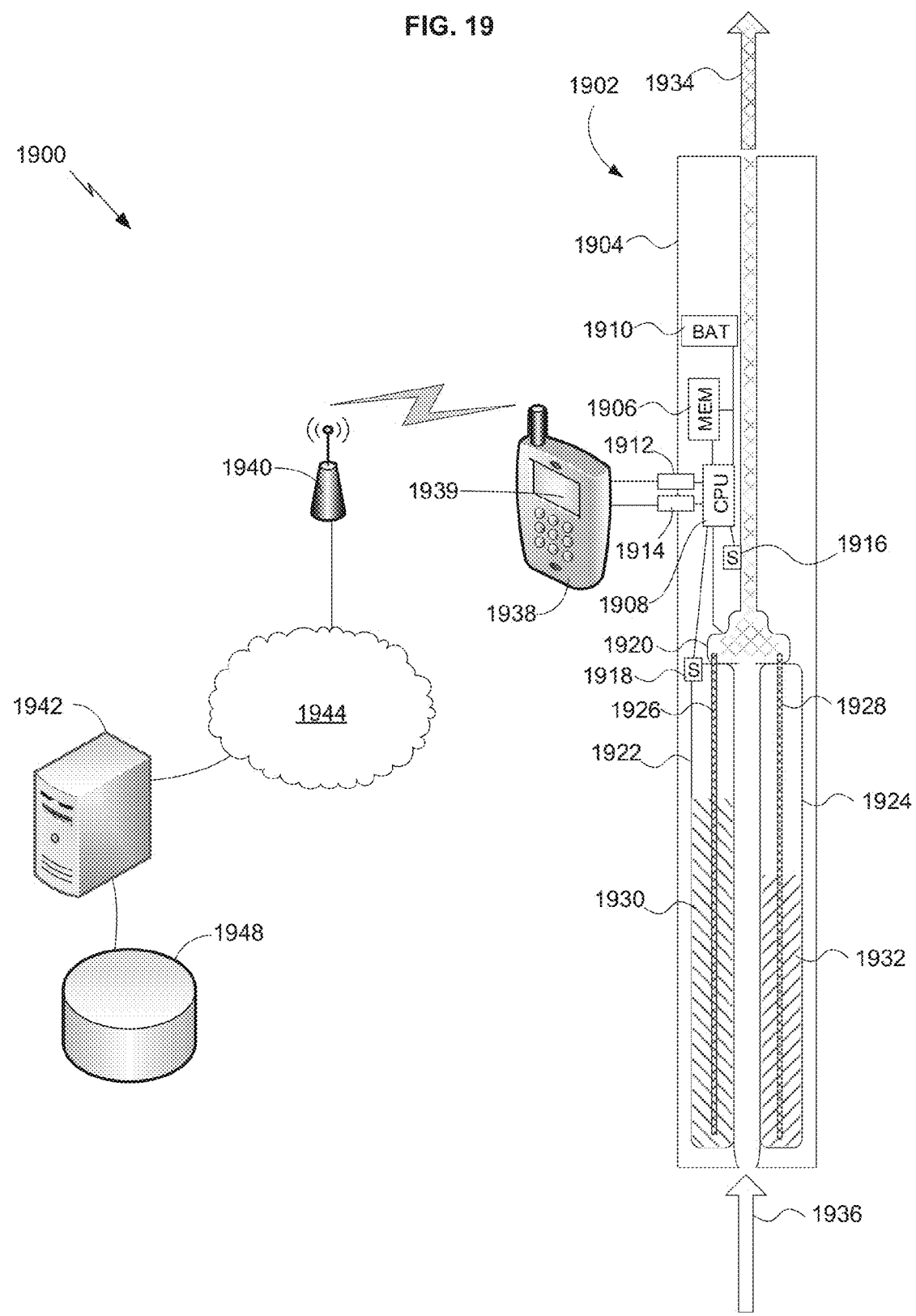
FIG. 19 illustrates an exemplary electronic vaporizer device.

Referring to FIG. 19, alternative aspects of a system 1900 for an intuitive user interface is illustrated. A single vapor device 1902 (also called a vaporizer or vaporizing device) is illustrated, but is should be appreciated that a recommendation system may include multiple such devices and ancillary equipment. The system 1900 may include an assembly 1902 for vaporizing a vaporizing fluid at a controlled rate, and optionally for combining vaporization of two or more different fluids in a controlled manner.

The assembly 1902 includes at least one container 1922 holding a vaporizable material 1930, sometimes referred to herein as a "first" container 1922 and "first" vaporizable material. In an aspect, the vaporizable material may be a fluid, such as a compressed gas, compressed liquid (e.g., a liquefied gas), or uncompressed liquid. Various suitable fluids are known in the art, for example, solutions of nicotine in glycerin, with or without flavor-enhancing agents, are known. In the alternative, or in addition, the first vaporizable material may be, or may include, a solid material. For embodiments using uncompressed liquids, the container 1922 may include a wick 1926 that carries the liquid to the vaporizing component 1920. Although the wick 1926 is shown only in the center of the container 1922 for illustrative clarity, it should be appreciated that the wick may substantially fill the container 1922. The container 1922 may be made of any suitable structural material, for example, an organic polymer, metal, ceramic, composite or glass material. Structural plastics may be preferred for disposable embodiments. Optionally, the apparatus 1902 may include one or more additional or "second" containers 1924 (one of potentially many shown), each configured similarly with a wick 1928 if suitable for the particular second vaporizable material 1932 being contained.

A vaporizer 1920 may be coupled to the first container 1922 and to any additional containers, e.g., second container 1924. For example, coupling may be via wicks 1926, 1924, via a valve, or by some other structure. The coupling mechanism may operate independently of gravity, such as by capillary action or pressure drop through a valve. The vaporizer 1920 is configured to vaporize the vaporizable material from the first container 1922 and any additional containers 1924 at controlled rates; in operation, the vaporizer vaporizes or nebulizes the material, producing an inhalable mist. In embodiments, the vaporizer may include a heater coupled to a wick, or a heated wick. A heating circuit may include a nickel-chromium wire or the like, with a temperature sensor (not shown) such as a thermistor or thermocouple. Within definable limits, by controlling suction-activated power to the heating element, a rate of vaporization may be controlled. At minimum, control may be provided between no power (off state) and one or more powered states. Other control mechanisms may also be suitable. The vaporizer can comprise one or more of a cooling element, a heating casing, and/or a magnetic element as described herein.

A processor 1908 is coupled to the vaporizer via an electrical circuit, configured to control a rate at which the vaporizer 1920 vaporizes the vaporizable material. In operation, the processor supplies a control signal to the vaporizer 1920 that controls the rate of vaporization. A receiver port 1912 is coupled to the processor, and the processor receives data determining the rate from the receiver port. Thus, the vaporization rate is remotely controllable, by providing the data. The processor 1908 may be, or may include, any suitable microprocessor or microcontroller, for example, a low-power application-specific controller (ASIC) designed for the task of controlling a vaporizer as described herein, or (less preferably) a general-purpose central processing unit, for example, one based on 80×86 architecture as designed by Intel™ or AMD™, or a system-on-a-chip as designed by ARM™ or other chip fabricator. The processor 1908 may be communicatively coupled to auxiliary devices or modules of the vaporizing apparatus 1902, using a bus or other coupling. Optionally, the processor 1908 and some or all of its coupled auxiliary devices or modules may be housed within or coupled to a housing 1904, substantially enclosing the containers 1924, 1924, the vaporizer 1920, the processor 1908, the receiver port 1912, and other illustrated components. The assembly 1902 and housing 1904 may be configured together in a form factor of an electronic cigarette, an electronic cigar, an electronic hookah, a hand-held personal vaporizer, or other desired form.

In related aspects, the assembly 1902 includes a memory device 1906 coupled to the processor 1908. The memory device 1906 may include a random access memory (RAM) holding program instructions and data for rapid execution or processing by the processor during control of the vaporizer 1902. When the vaporizer 1902 is powered off or in an inactive state, program instructions and data may be stored in a long-term memory, for example, a non-volatile magnetic, optical, or electronic memory storage device, which is not separately shown. A controlled rate or measured rate of vaporization, material vaporizes, times of use, and other data may be stored in the device memory 1906 and/or provided and stored by an ancillary device 1938 or server 1942 in data store 1948.

Either or both of the RAM or the storage device may comprise a non-transitory computer-readable medium holding program instructions, that when executed by the processor 1908, cause the apparatus 1902 to perform a method or operations as described herein. Program instructions may be written in any suitable high-level language, for example, C, C++, C#, or Java™, and compiled to produce machine-language code for execution by the processor. Program instructions may be grouped into functional modules, to facilitate coding efficiency and comprehensibility. It should be appreciated that such modules, even if discernable as divisions or grouping in source code, are not necessarily distinguishable as separate code blocks in machine-level coding. Code bundles directed toward a specific type of function may be considered to comprise a module, regardless of whether or not machine code on the bundle can be executed independently of other machine code. In other words, the modules may be high-level modules only.

In a related aspect, the processor 1908 receives a user identifier and stores the user identifier in the memory device 1906. A user identifier may include or be associated with user biometric data, that may be collected by a biometric sensor or camera included in the assembly 1902 or in a connected or communicatively coupled ancillary device 1938, such as, for example, a smart phone executing a vaporizer interface application. The processor 1908 may generate data indicating a quantity of the vaporizable material 1930, 1932 consumed by the vaporizer 1920 in a defined period of time, and save the data in the memory device 1906. The processor 1908 and other electronic components may be powered by a suitable battery 1910, as known in the art, or other power source. A user identifier may be associated by a server 1942 with use data gathered via the communication network 1940, 1944 from the vaporizer 1902. The server 1942 may identify users with similar use profiles by comparing use data from data store 1948. The server 1942, or a coupled server, may provide the user with use data via a recommendation network interface that can be browsed via a smart phone or other ancillary device 1938. In addition, the user may use the recommendation network to connect with other users with similar use profiles.

The assembly 1902 may optionally include a sensor 1916, or multiple sensors 1916, 1918, to provide measurement feedback to the processor. For example, a sensor 1916 may be positioned downstream of the vaporizer, and the processor may derive the data used for controlling vaporization rate at least in part by interpreting a signal from the sensor correlated to a composition of vapor, a quantity of vapor, a density of vapor, or some combination of such qualities of the vapor emitted by the vaporizer. For further example, a sensor 1918 positioned upstream of the vaporizer, and the processor may derive the data at least in part by interpreting a signal from the sensor correlated to a composition of the vaporizable material 1930 contained in the container 1922, an amount of the vaporizable material remaining in the container, or to an amount of the vaporizable material passed from the container to the vaporizer, or some combination of such measurements. "Downstream" and "upstream" relate to the direction of air flow or air/vapor mixture flow through the apparatus 1902, as illustrated by discharge arrow 1934 and inlet 1936. Suction applied at a tip draws inlet air 1936 through the vaporizer 1920, discharging a vapor/air mixture 1935 at the tip. Sensors 1916, 1918 may include, for example, optical sensors, temperature sensors, motion sensors, flow speed sensors, microphones or other sensing devices.

The processor 1908 may derive test and analysis data from the sensor 1916, 1918 signals. In the alternative, or in addition, the processor 1908 may send sensor data to a remote server 1942 or ancillary device 1939 using communication channels as described below. The server 1942 and/or ancillary device 1939 may analyze and compile provided sensor data from the vaporizer 1902 and/or multiple other vaporizers, and output test and analysis to a user interface such as a remotely accessible web page, graphical user interface of a local application, or output device (e.g., electronic display or audio transducer) included in the vaporizer 1902.

In related aspects, the assembly may include a transmitter port 1914 coupled to the processor. The memory 1906 may hold a designated network address, and the processor 1908 may provide data indicating the quantity of the vaporizable material consumed by the vaporizer to the designated network address in association with the user identifier, via the transmitter port 1914. Other data may include times and durations of use, type of vaporizable material consumed, and other data.

An ancillary device, such as a smartphone 1938, tablet computer, or similar device, may be coupled to the transmitter port 1914 via a wired or wireless coupling. For example, the apparatus 1902 may include a serial port, for example a USB port, coupled to receiver and transmitter inputs to the processor 1908. In the alternative, or in addition, a wireless port (not shown) using Wi-Fi (IEEE 802.11), Bluetooth, infrared, or other wireless standard may be coupled to the processor 1908. The ancillary device 1938 may be coupled to the processor 1908 for providing user control input to vaporizer control process operated executing on the processor 1908. User control input may include, for example, selections from a graphical user interface or other input (e.g., textual or directional commands) generated via a touch screen, keyboard, pointing device, microphone, motion sensor, camera, or some combination of these or other input devices, which may be incorporated in the ancillary device 1938. A display 1939 of the ancillary device 1938 may be coupled to the processor 1902, for example via a graphics processing unit (not shown) integrated in the ancillary device 1938. The display 1939 may include, for example, a flat screen color liquid crystal (LCD) display illuminated by light-emitting diodes (LEDs) or other lamps, a projector driven by an LED display or by a digital light processing (DLP) unit, or other digital display device. User interface output driven by the processor 1908 may be provided to the display device 1939 and output as a graphical display to the user. Similarly, an amplifier/speaker or other audio output transducer of the ancillary device 1938 may be coupled to the processor 1908 via an audio processing system. Audio output correlated to the graphical output and generated by the processor 1908 in conjunction with the ancillary device 1938 may be provided to the audio transducer and output as audible sound to the user.

The ancillary device 1938 may be communicatively coupled via an access point 1940 of a wireless telephone network, local area network (LAN) or other coupling to a wide area network (WAN) 1944, for example, the Internet. A server 1942 may be coupled to the WAN 1944 and to a database 1948 or other data store, and communicate with the apparatus 1902 via the WAN and couple device 1939. In alternative embodiments, functions of the ancillary device 1939 may be built directly into the apparatus 1902, if desired.

In related aspects, the processor 1908 may transmit measured or specified use data to the device 1938, which may relay the data to the server 1942 for providing, distributing, and sharing recommendation data in the network. For privacy protection, the server 1942 may delete the data after analysis to identify a common interest or use pattern for identifying like users. The server may protect use data from disclosure unless authorized by a user of the device 1902. The system 1900 may be used to implement a recommendation system as described herein. Other, similar systems may also be suitable.

Figure 20:
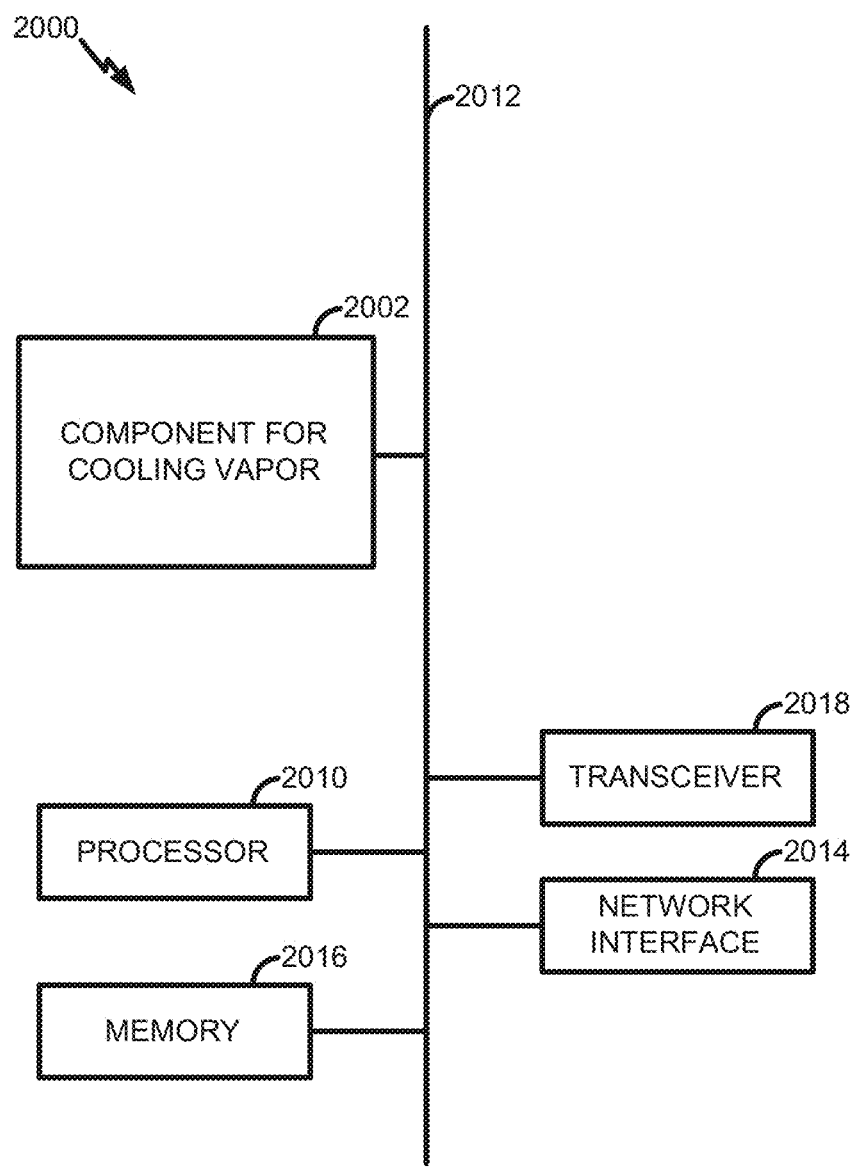
FIG. 20 illustrates an exemplary electronic vaporizer device.

FIG. 20 is a block diagram illustrating components of an apparatus or system 2000 for vapor cooling, in accord with the foregoing examples. The apparatus or system 2000 may include additional or more detailed components as described herein. For example, the processor 2010 and memory 2016 may contain an instantiation of a controller for a testing device as described herein. As depicted, the apparatus or system 2000 may include functional blocks that can represent functions implemented by a processor, software, or combination thereof (e.g., firmware).

As illustrated in FIG. 20, the apparatus or system 2000 may comprise an electrical component 2002 for vapor cooling. The component 2002 may be, or may include, a means for cooling vapor. Said means may include a coil and/or a cooling element coupled to a vaporizer.

The apparatus 2000 may include a processor module 2010 having at least one processor, in the case of the apparatus 2000 configured as a controller configured to operate transceiver 2018. The processor 2010, in such case, may be in operative communication with the memory 2016, interface 2014 or transceiver 2018 via a bus 2012 or similar communication coupling. The processor 2010 may effect initiation and scheduling of the processes or functions performed by electrical component 2002.

In related aspects, the apparatus 2000 may include a network interface module operable for communicating with a server over a computer network. The apparatus may include a transceiver 2018 for transmitting and receiving information to/from a server. In further related aspects, the apparatus 2000 may optionally include a module for storing information, such as, for example, a memory device/module 2016. The computer readable medium or the memory module 2016 may be operatively coupled to the other components of the apparatus 2000 via the bus 2012 or the like. The memory module 2016 may be adapted to store computer readable instructions and data for enabling the processes and behavior of the module 2002, and subcomponents thereof, or of the methods disclosed herein. The memory module 2016 may retain instructions for executing functions associated with the module 2002. While shown as being external to the memory 2016, it is to be understood that the module 2002 can exist within the memory 2016.

Figure 21:
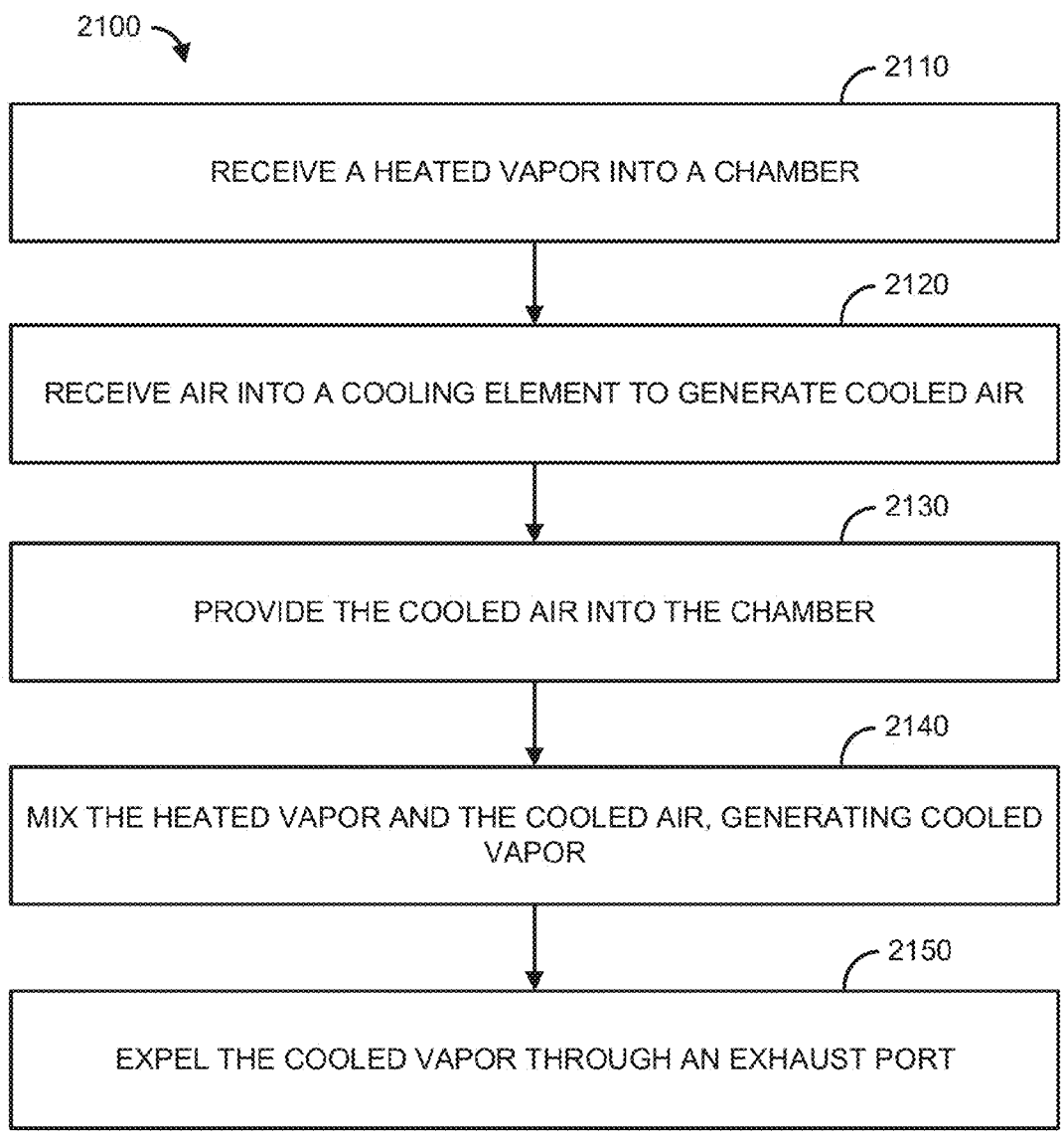
FIG. 21 illustrates an exemplary method.

In an aspect, illustrated in FIG. 21, disclosed is a method 2100 comprising receiving a heated vapor into a chamber at 2110. The heated vapor can be received from a mixing chamber of a vapor device and/or vaporizer as described herein. Air can be received into a cooling element to generate cooled air at 2120. The cooled air can be provided into the chamber at 2130. The heated vapor and the cooled air can be mixed, generating cooled vapor at 2140. The cooled vapor can be expelled through an exhaust port at 2150 for inhalation by a user or to cool an area near the exhaust port. A user can inhale the cooled vapor from the exhaust port through an inhalation port, a tube, a mouthpiece, or device end. The method 2100 can be performed by, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like.

In an aspect, the cooling element can comprise one or more of, a coil, a cooling grid, a cylindrical structure, a single cooled element, an airlock system, or any combination thereof. In another aspect, the cooling element can comprise one or more of, a chemical cooling system or a liquid cooling system. The chemical cooling system can comprise a container comprising ammonium nitrate in water or other chemical reaction.

The method can further comprise receiving a selection of a desired temperature and modifying performance of the cooling element based on the selected desired temperature. For example, a local and/or a remote user can select a desired temperate for vapor expelled from a vapor device. The local and/or remote user can utilize a local and/or a remote interface to make the selection. The local and/or remote interface can comprise one or more buttons, switches, dials, GUIs, combinations thereof and the like. Modifying the performance of the cooling element based on the selected desired temperature can comprise one or more of, limiting and/or increasing the amount of cooled air provided into the chamber, moving the cooling element closer to or further from the exhaust port, adjusting an amount of insulation covering the cooling element, combinations thereof and the like.

Figure 22:
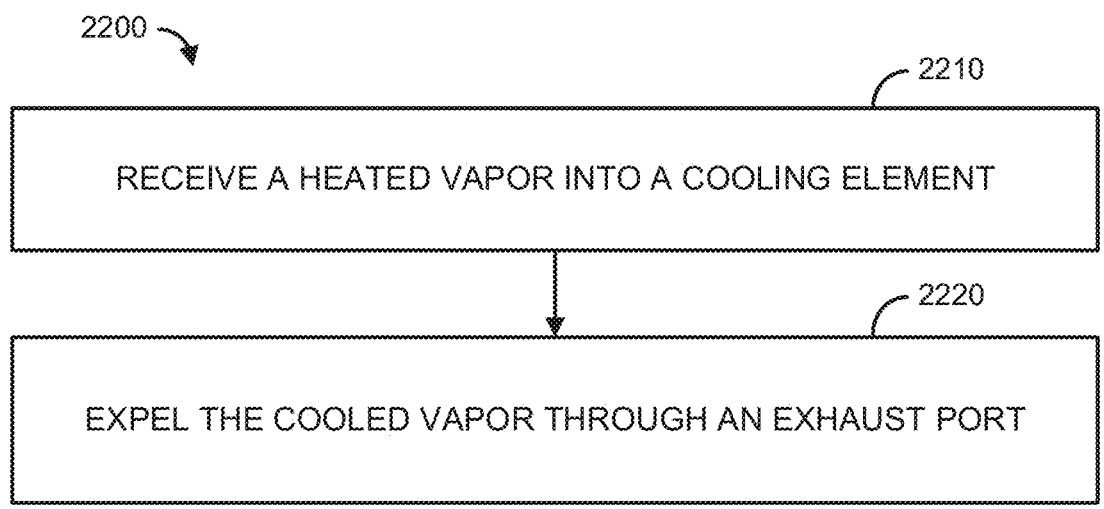
FIG. 22 illustrates an exemplary method.

In another aspect, illustrated in FIG. 22, disclosed is a method 2200 comprising receiving a heated vapor into a cooling element at 2210 and expelling the cooled vapor through an exhaust port at 2220. A user can inhale the cooled vapor from the exhaust port through an inhalation port, a tube, a mouthpiece, or device end. The method 2200 can be performed by, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like.

In an aspect, the cooling element can comprise one or more of, a coil, a cooling grid, a cylindrical structure, a single cooled element, an airlock system, or any combination thereof. In another aspect, the cooling element can comprise one or more of, a chemical cooling system or a liquid cooling system. The chemical cooling system can comprise a container comprising ammonium nitrate in water or other chemical reaction.

The method can further comprise receiving a selection of a desired temperature and modifying performance of the cooling element based on the selected desired temperature. For example, a local and/or a remote user can select a desired temperate for vapor expelled from a vapor device. The local and/or remote user can utilize a local and/or a remote interface to make the selection. The local and/or remote interface can comprise one or more buttons, switches, dials, GUIs, combinations thereof and the like. Modifying the performance of the cooling element based on the selected desired temperature can comprise one or more of, limiting and/or increasing the amount of cooled air provided into the chamber, moving the cooling element closer to or further from the exhaust port, adjusting an amount of insulation covering the cooling element, combinations thereof and the like.

In an aspect, an apparatus is disclosed comprising an air intake, a vapor output, a container for storing a vaporizable material, a mixing chamber coupled to the air intake for receiving air, the container for receiving the vaporizable material, and a heating element configured for heating the vaporizable material and the received air to generate a heated vapor, and a cooling element coupled to the mixing chamber, configured for receiving and cooling the heated vapor and providing the cooled vapor to the vapor output.

The cooling element can comprise one or more of, a coil, a cooling grid, a cylindrical structure, a single cooled element, an airlock system, or any combination thereof. The cooling element can comprise one or more of, a chemical cooling system or a liquid cooling system. The chemical cooling system comprises a container comprising ammonium nitrate in water. The apparatus can further comprise a user input interface for receiving a selection of a desired temperature and a processor for modifying performance of the cooling element based on the selected desired temperature. The apparatus can comprise an e-cigarette, an e-cigar, an electronic vapor modified device, a hybrid electronic communication handset coupled/integrated vapor device, a micro-sized electronic vapor device, or a robotic vapor device.

In an aspect, an apparatus is disclosed comprising an air intake, a vapor output, a container for storing a vaporizable material, a mixing chamber coupled to the air intake for receiving air, the container for receiving the vaporizable material, and a heating element configured for heating the vaporizable material and the received air to generate a heated vapor, and a cooling element coupled to the air intake, configured for receiving and cooling air and providing the cooled air to the vapor output wherein the cooled air mixes with the heated vapor, resulting in cooled vapor.

The cooling element can comprise one or more of, a coil, a cooling grid, a cylindrical structure, a single cooled element, an airlock system, or any combination thereof. The cooling element can comprise one or more of, a chemical cooling system or a liquid cooling system. The chemical cooling system comprises a container comprising ammonium nitrate in water. The apparatus can further comprise a user input interface for receiving a selection of a desired temperature and a processor for modifying performance of the cooling element based on the selected desired temperature.

The apparatus can comprise an e-cigarette, an e-cigar, an electronic vapor modified device, a hybrid electronic communication handset coupled/integrated vapor device, a micro-sized electronic vapor device, or a robotic vapor device.

In view of the exemplary systems described supra, methodologies that can be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks can be required to implement the methodologies described herein. Additionally, it should be further appreciated that the methodologies disclosed herein are capable of being stored on an article of manufacture to facilitate transporting and transferring such methodologies to computers.

Those of skill would further appreciate that the various illustrative logical blocks, modules, circuits, and algorithm steps described in connection with the aspects disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component," "module," "system," and the like are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components may reside within a process and/or thread of execution and a component can be localized on one computer and/or distributed between two or more computers.

As used herein, a nebulizing device uses oxygen, compressed air or ultrasonic power to break up medical solutions and suspensions into small aerosol droplets that may be directly inhaled from a mouthpiece of the device. It may be electronic and battery powered as well known in the art. The definition of an "aerosol" as used herein is a "mixture of gas and liquid particles," and the best example of a naturally occurring aerosol is mist, formed when small vaporized water particles mixed with hot ambient air are cooled down and condense into a fine cloud of visible airborne water droplets.

As used herein, a "vapor" includes mixtures of a carrier gas or gaseous mixture (for example, air) with any one or more of a dissolved gas, suspended solid particles, or suspended liquid droplets, wherein a substantial fraction of the particles or droplets if present are characterized by an average diameter of not greater than three microns. As used herein, an "aerosol" has the same meaning as "vapor," except for requiring the presence of at least one of particles or droplets. A substantial fraction means 10% or greater; however, it should be appreciated that higher fractions of small (<3 micron) particles or droplets can be desirable, up to and including 100%. It should further be appreciated that, to simulate smoke, average particle or droplet size can be less than three microns, for example, can be less than one micron with particles or droplets distributed in the range of 0.01 to 1 micron. A vaporizer may include any device or assembly that produces a vapor or aerosol from a carrier gas or gaseous mixture and at least one vaporizable material. An aerosolizer is a species of vaporizer, and as such is included in the meaning of vaporizer as used herein, except where specifically disclaimed.

Various aspects presented in terms of systems can comprise a number of components, modules, and the like. It is to be understood and appreciated that the various systems may include additional components, modules, etc. and/or may not include all of the components, modules, etc. discussed in connection with the figures. A combination of these approaches can also be used.

In addition, the various illustrative logical blocks, modules, and circuits described in connection with certain aspects disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein can be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor can read information from, and write information to, the storage medium. In the alternative, the storage medium can be integral to the processor. The processor and the storage medium may reside in an ASIC or may reside as discrete components in another device.

Furthermore, the one or more versions can be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Those skilled in the art will recognize many modifications can be made to this configuration without departing from the scope of the disclosed aspects.

The previous description of the disclosed aspects is provided to enable any person skilled in the art to make or use the present disclosure. Various modifications to these aspects will be readily apparent to those skilled in the art, and the generic principles defined herein can be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. An electronic vapor device comprising:
a device processor operable for controlling the electronic vapor device;
at least one container configured to store a vaporizable material;
a mixing component operatively coupled to the device processor and controlled in part by the device processor, wherein the mixing component is in fluid communication with the at least one container for receiving at least a portion of the vaporizable material therefrom, wherein the mixing component is operable to withdraw a selected amount of vaporizable material from the at least one container;
a vaporizing component operatively coupled to the device processor and controlled in part by the device processor, wherein the vaporizing component is in fluid communication with the mixing component for receiving at least a portion of the selected amount of vaporizable material withdrawn from the at least one container by the mixing component, wherein the vaporizing component is operable to vaporize the vaporizable material received therein;
at least one vapor outlet coupled to the vaporizing component and configured to receive vapor generated by the vaporizing component, the at least one vapor outlet operable to expel the generated vapor from the electronic vapor device;
a cooling component operatively coupled to the device processor and controlled in part by the device processor, wherein the cooling component is in fluid communication with the vaporizing component for receiving, at least a portion of vapor generated therein, wherein the cooling component is operable to cool at least a portion of the vapor received therein to a predetermined temperature, wherein the cooling component is coupled to the at least one vapor outlet for expelling cooled vapor therefrom; and
at least one power source operatively coupled to at least one of the mixing component, the vaporizing component, and the cooling component, wherein the at least one power source is operable to generate a supply of power for operation of at least one of the mixing component, the vaporizing component, the cooling component, and combinations thereof.

2. The electronic vapor device of claim 1, wherein the cooling component is selected from the group of cooling components consisting of at least one of: a coil, a cooling grid, a cylindrical structure, a chemical cooling element, a liquid cooling element, an air cooling element, and combinations thereof.

3. The electronic vapor device of claim 2, wherein the cooling component is comprised of at least one of: a metal, a liquid, a polymer, a natural substance, a synthetic substance, air, and combinations thereof.

4. The electronic vapor device of claim 2, wherein the device processor is operable to:
obtain data associated with at least one of at least one operational parameter of the mixing component, at least one operational parameter of the vaporizing component, at least one operational parameter of the cooling component, at least one characteristic of at least one vaporizable material contained in the at least one container, user data associated with at least one user of the electronic vapor device, and combinations thereof;
determine, in response to at least a portion of the obtained data, at least one device configuration for vaporizing at least one vaporizable material contained in the at least one container; and
generate at least one control signal for controlling at least one operation parameter of the electronic vapor device in accordance with the at least one device configuration.

5. The electronic vapor device of claim 4, wherein the device processor is further operable to generate at least one mixing control signal for controlling an amount of vaporizable material to be withdrawn from the at least one container.

6. The electronic vapor device of claim 4, wherein the device processor is further operable to generate at least one vaporizing control signal for controlling at least one vaporization parameter for vaporizing at least one vaporizable material withdrawn from the at least one container.

7. The electronic vapor device of claim 4, wherein the device processor is further operable to generate at least one cooling control signal for controlling at least one cooling parameter of the cooling component for cooling at least a portion of vapor generated by the vaporizing component.

8. The electronic vapor device of claim 4, further comprising an input/output device operatively coupled to the device processor and controlled in part by the device processor, wherein the input/output device is configured to receive a plurality of commands for controlling at least one operational parameter of the electronic vapor device for at least one of vaporizing at least one vaporizing material, cooling at least a portion of generated vapor, and combinations thereof, and to transmit the plurality of commands to the device processor;
wherein the device processor is operable to generate at least one control signal for controlling at least one operational parameter of the electronic vapor device in accordance with at least one command of the plurality of commands.

9. The electronic vapor device of claim 8, wherein the input/output device comprises a user interface, wherein the device processor is operable to receive at least a portion of the plurality of commands from an associated user via the user interface.

10. The electronic vapor device of claim 1, wherein the electronic vapor device is selected from the group of electronic vapor devices consisting of: an electronic cigarette, an electronic cigar, an electronic vapor device, an electronic vapor device integrated with an electronic communication device, a robotic vapor device, and a micro-size electronic vapor device.

11. A method for vaporizing at least one vaporizable material by electronic vapor device, wherein the electronic vapor device comprises (a) a device processor for controlling the electronic vapor device, (b) at least one container configured to store a vaporizable material, (c) a mixing component operable to control a selected amount of vaporizable material to be withdrawn from the at least one container, (d) a vaporizing component operable to vaporize a plurality of materials received therein and expel a generated vapor from the vaporizing component, (e) a cooling component operable to cool at least a portion of generated vapor received therein to a predetermined temperature, and (f) at least one power source operatively coupled to the mixing component and the vaporizing component, the method comprising:
receiving, at the device processor, at least one command to activate the electronic vapor device;

generating, by the device processor, at least one control signal for controlling at least one operational parameter of the electronic vapor device in accordance with the at least one command;

withdrawing, by the mixing component, a selected amount of vaporizable material from the at least one container in accordance with the at least one control signal and delivering the selected amount of vaporizable material withdrawn therefrom to the vaporizing component;

vaporizing at least a portion of the selected amount of vaporizable material by the vaporizing component in accordance with the at least one control signal to generate vapor therefrom and transferring at least a portion of the generated vapor to the cooling component; and cooling, by the cooling component, at least a portion of vapor received therein to a predetermined temperature and delivering the cooled vapor to the at least one vapor outlet for outputting therefrom.

12. The method of claim 11, wherein at least a portion of the generated vapor is cooled via at least one of: a chemical cooling process, a liquid cooling process, an air cooling process, a mechanical cooling process, and combinations thereof.

13. The method of claim 11, further comprising:

obtaining data associated with at least one of at least one operational parameter of the mixing component, at least one operational parameter of the vaporizing component, at least one operational parameter of the cooling component, at least one characteristic of at least one vaporizable material contained in the at least one container, user data associated with at least one user of the electronic vapor device, and combinations thereof;

determining, in response to at least a portion of the obtained data, at least one device configuration for vaporizing at least one vaporizable material contained in the at least one container; and generating at least one control signal for controlling at least one operational parameter of the electronic vapor device in accordance with the at least one device configuration.

14. The method of claim 13, further comprising generating at least one mixing control signal for controlling an amount of vaporizable material to be withdrawn from the at least one container.

15. The method of claim 13, further comprising generating at least one vaporizing control signal for controlling at least one vaporization parameter for vaporizing at least one vaporizable material withdrawn from the at least one container.

16. The method of claim 13, further comprising generating at least one cooling control signal for controlling at least one cooling parameter of the cooling component for cooling at least a portion of vapor generated by the vaporizing component.

17. The method of claim 13, wherein the electronic vapor device further comprises an input/output device, the method further comprising:

receiving, via the input/output device, a plurality of commands for controlling at least one operational parameter of the electronic vapor device for at least one of vaporizing at least one vaporizing material, cooling at least a portion of generated vapor, and combinations thereof;

transmitting the plurality of received commands to the device processor; and generating, by the device processor, at least one control signal for controlling at least one operational parameter of the electronic vapor device in accordance with at least one command of the plurality of commands.

18. The method of claim 17, wherein at least a portion of the plurality of commands are received from an associated user via a user interface.

* * * * *